US008715962B2

(12) United States Patent
Alvizo et al.

(10) Patent No.: US 8,715,962 B2
(45) Date of Patent: May 6, 2014

(54) PRODUCTION OF GERANYL DIPHOSPHATE

(75) Inventors: Oscar Alvizo, Fremont, CA (US);
Robert McDaniel, Palo Alto, CA (US);
Benjamin Mijts, Belmont, CA (US)

(73) Assignee: Codexis, Inc., Redwood City, CA (US)

( * ) Notice: Subject to any disclaimer, the term of this patent is extended or adjusted under 35 U.S.C. 154(b) by 41 days.

(21) Appl. No.: 13/577,715

(22) PCT Filed: Mar. 30, 2011

(86) PCT No.: PCT/US2011/030590
§ 371 (c)(1),
(2), (4) Date: Aug. 8, 2012

(87) PCT Pub. No.: WO2011/123567
PCT Pub. Date: Oct. 6, 2011

(65) Prior Publication Data
US 2013/0011888 A1  Jan. 10, 2013

Related U.S. Application Data

(60) Provisional application No. 61/319,586, filed on Mar. 31, 2010, provisional application No. 61/319,560, filed on Mar. 31, 2010.

(51) Int. Cl.
*C12N 15/52* (2006.01)
*C12N 15/11* (2006.01)
*C12N 15/09* (2006.01)

(52) U.S. Cl.
USPC .......... 435/69.1; 435/166; 435/67; 435/252.1

(58) Field of Classification Search
USPC ........................................... 435/69.1, 166, 67
See application file for complete search history.

(56) References Cited

U.S. PATENT DOCUMENTS

| | | | |
|---|---|---|---|
| 5,885,810 | A | 3/1999 | Ohto et al. |
| 6,117,679 | A | 9/2000 | Stemmer |
| 6,225,096 | B1 | 5/2001 | Narita et al. |
| 6,303,330 | B1 | 10/2001 | Croteau et al. |
| 6,376,246 | B1 | 4/2002 | Crameri et al. |
| 6,395,525 | B2 | 5/2002 | Ohto et al. |
| 6,586,182 | B1 | 7/2003 | Patten et al. |
| 6,806,076 | B1 | 10/2004 | Miyake et al. |
| 6,818,424 | B2 | 11/2004 | DiCosimo et al. |
| 7,629,157 | B2 | 12/2009 | Davis et al. |
| 2001/0051359 | A1 | 12/2001 | Ohto et al. |
| 2004/0131637 | A1 | 7/2004 | Chatfield |
| 2008/0220990 | A1 | 9/2008 | Fox |
| 2009/0312196 | A1 | 12/2009 | Colbeck et al. |

FOREIGN PATENT DOCUMENTS

| | | |
|---|---|---|
| EP | 0 821 065 B1 | 3/2007 |
| WO | 95/22625 | 8/1995 |
| WO | 96/17951 | 6/1996 |
| WO | 97/20078 | 6/1997 |
| WO | 97/35966 | 10/1997 |
| WO | 98/27230 | 6/1998 |
| WO | 00/42651 | 7/2000 |
| WO | 01/75767 | 10/2001 |
| WO | 2005/017135 | 2/2005 |
| WO | 2007/139924 | 12/2007 |

OTHER PUBLICATIONS

NCBI Accession No. NP_179998,1, myrcene/ocimene synthase [*Arabidopsis thaliana*], downloaded on Feb. 19, 2013.
Needleman, S.B., et al., "A General Method Applicable to the Search for Similarities in the Amino Acid Sequence of Two Proteins,", J. Mol. Biol., 48:443-453 [1970].
Ohnuma, S. et al. "Conversion from Farnesyl Diphosphate Synthase to Geranylgeranyl Diphosphate Synthase by Random Chemical Mutagenesis," J. Biol. Chem., 271(17)10087-957 [1996].
Ohnuma, S., et al., "Conversion of Product Specificity of Archaebacterial Geranylgeranyl-diphosphate Synthase," J. Biol. Chem., 271(31):18831-37 [1996].
Ortiz, A.R., et al., "Computational Approaches to Model Ligand Selectivity in Drug Design," Curr Top Med Chem., 6(1):41-55 [2006].
Pulkkinen, W.S., "A *Salmonella typhimurium* Virulence Protein is Similar to a *Yersinia enterocolitica* Invasion Protein and a Bacteriophage Lambda Outer Membrane Protein," J. Bacteriol., 173(1): 86-93 [1991].
Reiling, K.K., et al., "Mono and Diterpene Productionin *Escherichia coli*," Biotechnology and Bioengineering, 87(2):200-212 [2004].
Schmidt, A., et al., "Cloning and characterization of two different types of geranyl diphosphate synthases from Norway spruce (*Picea abies*)," Phytochemisty 69:49-57 [2008].
Shetron-Rama, L.M., et al., "Intracellular Induction of *Listeria monocytodenes* actA Expression," Infect. Immun., 70(3):1087-1096 [2002].
Smith, M., "In Vitro Mutagenesis," Ann. Rev. Genet., 19:423-462 [1985].
Stemmer, W.P.C., "DNA shuffling by random fragmentation and reassembly: In vitro recombination for molecular evolution," Proc. Nat. Acad. Sci. USA, 91:10747-10751 [1994].
Stemmer, W.P.C., "Rapid evolution of a protein in vitro by DNA shuffling" Nature, 370:389-391 [1994].
Tarshis, L.C., et al., "Regulation of product chain length by isoprenyl diphosphate synthases," PNAS,93:15018-15023 [1996].
Valdivia, R.H., et al., "Bacterial genetics by flow cytometry: rapid isolation of *Salmonella typhimurium* acid-inducible promoters by differential fluorescence induction," Mol. Microbiol 22(2):367-378 [1996].
Vandermoten S., et al, "Charactizaton of a novel aphid prenyltransferase displaying dual geranyl/farnesyl diphosphate synthase activity," FEBS Letters, 582:1928-1934 [2008].
Wells, J.A., et al., "Cassette mutagenesis: an efficient method for generation of multiple mutations at defined sites," Gene, 34:315-323 [1985].

(Continued)

*Primary Examiner* — Kagnew H Gebreyesus
(74) *Attorney, Agent, or Firm* — Codexis, Inc.

(57) ABSTRACT

The invention relates to recombinant geranyl diphosphate (GPP) synthases, genes encoding the synthases, vectors and host cells comprising the same. More particularly, the invention relates to a recombinant GPP synthase, which preferentially facilitates the production of GPP from its isoprenoid precursors and incorporating a recombinant GPP synthase into one or more terpene production pathways of a host organism.

26 Claims, 7 Drawing Sheets

(56) References Cited

OTHER PUBLICATIONS

Yuba, A., et al., "cDNA Cloning, Characterization, and Functional Expression of 4S-(−)-Limonene Synthase from *Perilla frutescens*," Arch Biochem Biophys, 332(21):280-287 [1996].

Zhang J.-H., et al., "Directed evolution of a fucosidase from a galactosidase by DNA shuffling and screening" Proc. Nat. Acad. Sci. U.S.A., 94:4504-4509 [1997].

Alpuche Arando, C.M., et al., "*Salmonella typhimurium* activates virulence gene transcription within acidified macrophage phagosomes," PNAS, 89(21): 10079-83 [1992].

Altschul, S.F., et al., "Basic Local Alignment Search Tool," J. Mol. Biol., 215: 403-410 [1990].

Altschul, S.F., et al., "Gapped Blast and PSI-Blast: a new generation of protein database search programs," Nucleic Acids Res., 25(17):3389-3402 [1997].

Arnold, F.H., "Combinatorial and computationalchallenges for biocatalyst design," Nature, 409(6817):253-7 [2001].

Badger, P., "Ethanol from Cellulose: A General Review," in J. Janick and A. Whipkey (eds.), Trends in New Crops and Uses, ASHS Press, pp. 17-21 [2002].

Bitter, G.A., "Heterologous Gene Expression in Yeast," Methods in Enzymology, Eds. Berger & Kimmel, Acad. Press, N,Y., 152:673-684 [1987].

Bitter, G.A., et al., "Expression and Secretion Vectors for Yeast," Methods in Enzymology, Eds. Berger & Kimmel, Acad. Press, N.Y., 153:516-544 [1987].

Botstein, D., et al., "Strategies and Applications of In Vitro Mutagenesis," Science, 229(4719):1193-1201 [1985].

Bouvier, F., et al., "Molecular cloning of geranyl diphosphate synthase and compartmentation of monoterpene synthesis in plant cells," The Plant Journal, 24(2):241-252 [2000].

Burke, C., et al, "Geranyl diphosphate synthase from *Abies grandis*: cDNA isolation, functional expression, and characterization", Archives of Biochemistry and Biophysics, 405:130-136 [2002].

Burke, C., et al, "Geranyl diphosphate synthase: Cloning, expression, and characterization of this prenyltransferase as a heterodimer," PNAS, 96(23):13062-13067 [1999].

Carter, P., "Site-directed mutagenesis," Biochem. J., 237:1-7 [1986].

Chatfield, S.N., et al., "Use of the nirB promoter to direct the stable expression of heterologous antigens in *Salmonella* oral vaccine strains: development of a single-dose oral tetanus vaccine," Biotechnology, 10:888-892 [1992].

Chica, R.A. et al., "Semi-rational approaches to engineering enzyme activity: combining the benefits of directed evolution and rational design,"Curr Opin Biotechnol., 16(4):378-84 [2005].

Christians, F.C., et al., "Directed evolution of thymidine kinase for AZT phosphorylation using DNA family shuffling," Nat. Biotechnol., 17:259-264 [1999].

Crameri A., et al., "DNA shuffling of a family of genes from diverse species accelerates directed evolution," Nature, 391:288-291 [1998].

Crameri, A., et al., "Improved green fluorescent protein by molecular evolution using DNA shuffling," Nat. Biotechnol., 14:315-319 [1996].

Crameri, A., et al., "Molecular evolution of an arsenate detoxification pathway by DNA shuffing" Nat. Biotechnol., 15:436-438 [1997].

Dale, S.J., et al., "Oligonucleotide-Directed Random Mutagenesis Using the Phosphorothioate Method," Meth. Mol. Biol., 57:369-74 [1996].

Damborsky, J., et al., "Computational tools for designing and engineering biocatalysts," Curr Opin Chem Biol.,13 (1):26-34 [2009].

Diaz, N., et al., "Kinetic and binding effects in peptidesubstrate selectivity of matrix metalloproteinase-2: Molecular dynamics and QM/MM calculations," Proteins, 78(1):1-11 [2010].

Dunstan, S.J., et al., "Use of In Vivo-Regulated Promoters to Deliver Antigens from Attenuated *Salmonella enterica* var. *Typhimurium*," Infect. Immun. 67(10):5133-5141 [1999].

Fernandez S.M.S., et al., "Farnesyl Diphosphate Synthase. Altering the Catalytic Site to Select for Geranyl Diphosphate Activity," Biochemistry, 39:15316-15321 [2000].

GenBank Accession Nos. AX798183, Sequence 59 from Patent WO03054201, downloaded Feb. 19, 2013.

GenBank Accession Nos. AX798961, Sequence 53 from Patent WO03054189, downloaded Feb. 19, 2013.

GenBank Accession Nos. AX798980, Sequence 72 from Patent WO03054189, downloaded Feb. 19, 2013.

Guzman, L.M.,et al., "Tight Regulation, Modulation, and High-Level Expression by Vectors Containing the Arabinose PBAD Promoter," J, Bacteriol., 177(14):4121-4130 [1995].

Harborne, N,R., et al., "Transcriptional control, transiation and function of the products of the five open reading frames of the *Escherichia coli* nir operon," Mol. Micro. 6[19]:2805-2813 [1992].

Henikoff, S., et al., "Amino acid substitution matrices from protein blocks," Proc. Natl. Acad. Sci. USA, 89:10915-10919 [1992].

Hoffmann, F., et al., "Heat-inactivation of plasmid-encoded CI857 repressor induces gene expression from Ind lambda prophage in recombinant *Escherichia coli*," FEMS Microbiol Lett., 177(2):327-34 [1999].

Kim, L., et al., "A xylose-inducible *Bacillus subtilis* integration vector and its application," Gene, 181:71-76 [1996].

Kramer, B., et al., "Different base/base mismatches are corrected with different efficiencies by methy-directed DNA mismatch-repair system of *E. coli*," Cell, 38:879-887 [1984].

Lee, P.C., et al., "Alteration of product specificity of *Aeropyrum pernix* farnesylgeranyl diphosphate synthase (Fgs) by directed evolution," Protein Eng. Des. Sel., 17:771-777 [2004].

Lee, P.C., et al., "Directed evolution of *Escherichia coli* farnesyl diphosphate synthase (IspA) reveals novel structural determinants of chain length specificity," Metab Eng., 7:18-26 [2005].

Ling, M.M., et al., "Approaches to DNA Mutagenesis: An Overview," Anal. Biochem., 254(2):157-78 [1997].

Lippow, S.M., et al., "Progress in computational protein design," Curr Opin Biotechnol., 18(4):305-11 [2007].

Martin V.J.J., et al., "Engineering a mevalonate pathway in *Escherichia coli* producton of terpenoids" Nature Biotech. 21(7):796-802 [2003].

McKelvie, N.D., et al., "Expression of heterologous antigens in *Salmonella Typhimurium* vaccine vectors using the in vivo-inducible, SPI-2 promoter, ssaG," Vaccine, 22:3243-3255 [2004].

Melton, D.A., et al., "Effcient in vitro synthesis of biologically active RNA and RNA hybridizaton probes from plasmids containing a bacteriophage SP6 promoter," Nucl. Acids Res., 12(18):7035-7056 [1984].

Meyer, M.M., et al., "Structure-guided SCHEMA recombination of distantly related beta-lactamases," Protein Eng Des Sel., 19(12):563-70 [2006].

Minshull, J., et al., "Protein evolution by molecular breeding," Current Opinion in Chemical Biology, 3:284-290 [1999].

Narita, K., et al., "Protein Design of Geranyl Diphosphate Synthase. Strutural Features That Define the Product Specificities of Prenyltransferases," J. Biochem., 126:566-571 [1999].

NCBI Accession No. AAB70707.1, (−)-camphene synthase [*Abies grandis*], downloaded on Feb. 19, 2013.

NCBI Accession No. AAC26017, (+)-bornyl diphosphate synthase [*Salvia officinalis*], downloaded on Feb. 19, 2013.

NCBI Accession No. AAC37366.1, 4S-limonene synthase [*Mentha spicata*], downloaded on Feb. 19, 2013.

NCBI Accession No. AAK58723.1, (−)-beta-pinene synthase [*Artemisia annua*], downloaded on Feb. 19, 2013.

NCBI Accession No. AAV63790.1, fenchol synthase [*Ocimum basilicum*], downloaded on Feb. 19, 2013.

NCBI Accession No. AAX07267.1, (−)-alpha-pinene/(−)-camphene synthase [*Pseudotsuga menziesii*], downloaded on Feb. 19, 2013.

NCBI Accession No. ABH07677.1, cineole synthase [*Salvia fruticosa*], downloaded on Feb. 19, 2013.

NCBI Accession No. ABP01684.1, pinene synthase [*Rosmarinus officinalis*], downloaded on Feb, 19, 2013.

FIG. 2

(A) WT ispA DNA sequence (Escherichia coli BW2952) (SEQ ID NO: 1)

```
ATGGACTTTC CGCAGCAACT CGAAGCCTGC GTTAAGCAGG CCAACCAGGC GCTGAGCCGT
TTTATCGCCC CACTGCCCTT TCAGAACACT CCCGTGGTCG AAACCATGCA GTATGGCGCA
TTATTAGGTG GTAAGCGCCT GCGACCTTTC CTGGTTTATG CCACCGGTCA TATGTTCGGC
GTTAGCACAA ACACGCTGGA CGCACCCGCT GCCGCCGTTG AGTGTATCCA CGCTTACTCA
TTAATTCATG ATGATTTACC GGCAATGGAT GATGACGATC TGCGTCGCGG TTTGCCAACC
TGCCATGTGA AGTTTGGCGA AGCAAACGCG ATTCTCGCTG GCGACGCTTT ACAAACGCTG
GCGTTCTCGA TTTTAAGCGA TGCCGATATG CCGGAAGTGT CGGACCGCGA CAGAATTTCG
ATGATTTCTG AACTGGCGAG CGCCAGTGGT ATTGCCGGAA TGTGCGGTGG TCAGGCATTA
GATTTAGACG CGGAAGGCAA ACACGTACCT CTGGACGCGC TTGAGCGTAT TCATCGTCAT
AAAACCGGCG CATTGATTCG CGCCGCCGTT CGCCTTGGTG CATTAAGCGC CGGAGATAAA
GGACGTCGTG CTCTGCCGGT ACTCGACAAG TATGCAGAGA GCATCGGCCT TGCCTTCCAG
GTTCAGGATG ACATCCTGGA TGTGGTGGGA GATACTGCAA CGTTGGGAAA ACGCCAGGGT
GCCGACCAGC AACTTGGTAA AAGTACCTAC CCTGCACTTC TGGGTCTTGA GCAAGCCCGG
AAGAAAGCCC GGGATCTGAT CGACGATGCC CGTCAGTCGC TGAAACAACT GGCTGAACAG
TCACTCGATA CCTCGGCACT GGAAGCGCTA GCGGACTACA TCATCCAGCG TAATAAATAA
```

(B) WT IspA amino acid sequence (SEQ ID NO: 2):

MDFPQQLEACVKQANQALSRFIAPLPFQNTPVVETMQYGALLGGKRLRPFLVYATGHMFGVSTNT
LDAPAAAVECIHAY<u>S</u>LIHDDLPAMDDDDLRRGLPTCHVKFGEANAILAGDALQTLAFSILSDADM
PEVSDRDRISMISELASASGIAGMCGGQALDLDAEGKHVPLDALERIHRHKTGALIRAAVRLGAL
SAGDKGRRALPVLDKYAESIGLAFQVQDDILDVVGDTATLGKRQGADQQLGKSTYPALLGLEQAR
KKARDLIDDARQSLKQLAEQSLDTSALEALADYIIQRNK (C) S80F IspA amino acid sequence (SEQ ID NO: 3):

MDFPQQLEACVKQANQALSRFIAPLPFQNTPVVETMQYGALLGGKRLRPFLVYATGHMFGVSTNT
LDAPAAAVECIHAY<u>F</u>LIHDDLPAMDDDDLRRGLPTCHVKFGEANAILAGDALQTLAFSILSDADM
PEVSDRDRISMISELASASGIAGMCGGQALDLDAEGKHVPLDALERIHRHKTGALIRAAVRLGAL
SAGDKGRRALPVLDKYAESIGLAFQVQDDILDVVGDTATLGKRQGADQQLGKSTYPALLGLEQAR
KKARDLIDDARQSLKQLAEQSLDTSALEALADYIIQRNK

FIG. 5: Alignment of wild-type *E. coli* IspA (SEQ ID NO: 2) with
*Avian* FPP Synthase (Gallus_gallus) (SEQ ID NO: 6)

```
Escherichia_coli    ----------MDFPQQLEACVKQANQALSRFIAPLPFQN----------------TPVV  33
Gallus_gallus       MHKFTGVNAKFQQPALRNLSPVVVEREREEFVGFFPQIVRDLTEDGIGHPEVGDAVARLK  60
                              :: *   :  .  .::  ..*:. :*                      : :

Escherichia_coli    ETMQYGALLGGKRLRPFLVYATGHMFG---VSTNTLDAPAAAVECIHAYSLIHDDLPAMD  90
Gallus_gallus       EVLQYNAPGGKCNRGLTVVAAYRELSGPGQKDAESLRCALAVGWCIELFQAFFLVADDIM 120
                    *.:**.*   *   :* *  .: *     .:::*  .. *.  **. :. :.      :

Escherichia_coli    DDDLRRGLPTCHVKFG--EANAILAGDALQTLAFSILSDADMPEVSDRDRISMISELASA 148
Gallus_gallus       DQSLTRRGQLCWYKKEGVGLDAINDSFLLESSVYRVLKKYCRQRPYYVHLLELFLQTAYQ 180
                    *:.* *    *  .*    :**  .  *::  .: :*..    .  . ..:: : *

Escherichia_coli    SGIAGMCGGQALDLD-AEGKHVPLDALERIHRHKTG-ALIRAAVRLGALSAGDKGRRALP 206
Gallus_gallus       TELGQMLDLITAPVSKVDLSHFSEERYKAIVKYKTAFYSFYLPVAAAMYMVGIDSKEEHE 240
                    : :. *  .  :   :. .:.*.. :  : * ::**.   : .*   .*  ...:.

Escherichia_coli    VLDKYAESIGLAFQVQDDILDVVGDTATLGKRQGADQQLGKSTYPALLGLEQARKKARDL 266
Gallus_gallus       NAKAILLEMGEYFQIQDDYLDCFGDPALTG-KVGTDIQDNKCSWLVVQCLQRVTPEQRQL 299
                       .:* **:*** ** .**.*  *  *:* * .*.:: .:  *::.   : *:*

Escherichia_coli    IDD--------------------ARQSLKQLAEQS--------------LDTSALEALA 291
Gallus_gallus       LEDNYGRKEPEKVAKVKELYEAVGMRAAFQQYEESSYRRLQELIEKHSNRLPKEIFLGLA 359
                    ::*                      * :::*  *.*              *  .. : .**

Escherichia_coli    DYIIQRNK 299
Gallus_gallus       QKIYKRQK 367
```

FIG. 6

```
IspA_E.coli       ---------------MDFPQQLEACVKQANQALSRFIAPLPFQNTPVVETMQYGALLGGKRL  47
YP_215451.1       ---------------MDFTQQLQACVTQANQALSRFIAPLPFQNTPVVEAMQYGALLGGKRL  47
YP_003209360.1    ---------------MDFSQQLQSQAERANSALQHFIGALPFQKSPLVEAMLYGTLLGGKRL  47
YP_049238.1       ---------------MTDFSAQLNAHYQRTNRMLGHFITSLPFQSSPLVNAMEYGSLLGGKRL  48
YP_002924367.1    MPDKISFSDQHTSFDFDQQLSKYQKRVETYLSSALDKLPAYNTVLLDVMRYSTLMGGKRL  60
YP_002796315.1    ----------MTDTDFLRWMTDIQQHVETALAASLPAGTHAATPLFDAMRYAALDGGKRV  50
NP_252732.1       ---------------MIAAYQARCQARVDAALDALFVAPREELQRLYEAMRYSVMNGGKRV  46
YP_088252.1       --------MMRLMYQFSNDLQQAQQRINRFLEAQFDEINTRPSPLADAMKYGLLLGGKRI  52
NP_245470.1       -------------MYQLSQDLPQLQQRINTFLAQQLN-VDSSPSPLAEAMRYGVLLGGKRI  47
                                :         :  :  *   :         : :.* *. : ****:

IspA_E.coli       RPFLVYATGHMFGVSTNTLDAPAAAVECIHAYSLIHDDLPAMDDDDLRRGLPTCHVKFGE  107
YP_215451.1       RPFLVYATGQMFGVSTATLDAPAAAVECIHAYSLIHDDLPAMDDDDLRRGLPTCHIKFGE  107
YP_003209360.1    RPFLVYATGEMFGVNPTALDAPAAAIECIHAYSLMHDDLPAMDDDDLRRGQPTCHIRFGE  107
YP_049238.1       RPFLVYTTGELFDMPLESLDAPAAAVECIHAYSLIHDDLPAMDDDDLRRGQPTCHIKFGE  108
YP_002924367.1    RPYLVYATGQMLGLSLSNLDAPAAAIECIHSYSLLHDDLPSMDNDDLRRGELTGHVKFGE  120
YP_002796315.1    RPLLVFAAGDVSGATPEALSAAACAVECIHAYSLVHDDLPCMDDDVLRRGKPTCHIAHGE  110
NP_252732.1       RPLLAYAACEALGGAPQRADAAACAVELIHAYSLVHDDLPAMDDDDLRRGQPTTHRAFDE  106
YP_088252.1       RPFLVYATGRMLGADTAQLDYAAAAIEAIHAYSLIHDDLPAMDNDSLRRGQPTCHIAFDH  112
NP_245470.1       RPFLVYATGRMLGADLNQLDYAAASVEAVHAYSLIHDDLPAMDDDHLRRGQPTCHIAFDH  107
                  ** *.::.       . .*.:* :*:***:*****.**:*  **** * *..

IspA_E.coli       ANAILAGDALQTLAFSILSDADMPEVSDRDRISMISELASASGIAGMCGGQALDLDAEGK  167
YP_215451.1       ANAILAGDALQALAFAIISDAPMPEVADRDRIAMIAELANASGIAGMCGGQALDLAAEGQ  167
YP_003209360.1    ASAILAGDALQTLAFSILSDAPMENVALRDRLAMVSELAKASGVAGMCGGQALDLEAEGQ  167
YP_049238.1       ATAILAGDALQTLAFSILADAPMTQVSDRDRLAMISELAQASGVAGMCGGQAFDLEAEGH  168
YP_002924367.1    ANAILAGDSLQSLAFSILADDRMPDVVTEDRLAMLSELARASGATGMCGGQALDMASEYL  180
YP_002796315.1    AMALLAGDALQAHAFELLAIPLPG-VVPARQLAMVSALAHAAGPRGMCGGQAIDLAAVGH  169
NP_252732.1       ATAILAADGLQALAFEVLADTRRNPQEHAVCLEMLTRLARAAGSAGMVGGQAIDLGSVGV  166
YP_088252.1       ATAILAGDALQAFAFEILT--KSTALSAEQKLRLIQVLSHNSGVFGMCLGQSLDLISEHK  170
NP_245470.1       ATAILAGDALQAFAFEILT--QAPALQAEQKLALVQTLSQAAGVKGMCLGQSLDLISEQK  165
                  * *:**.*.**: **  :::             : ::  *:  :* **  **::*:  :

IspA_E.coli       HVPLDALERIHRHKTGALIRAAVRLGALSAGDKGRRALP-VLDKYAESIGLAFQVQDDIL  226
YP_215451.1       RITLDALERIHRHKTGALIRAAVRLGALSAGDKGRNTLP-ILDRYAESIGLAFQVQDDIL  226
YP_003209360.1    QVDLDALERIHRHKTGALIRAAVRMGALCAGDKGRDALV-YLDSYAESIGLAFQVQDDIL  226
YP_049238.1       QVNLAALERIHRHKTGALIRAAVRLGALAAGDAGRDALP-YLDRYANAIGLAFQVQDDIL  227
YP_002924367.1    DISLETLELIHHHKTGALLRAAVRLGALAAGETGRKALP-WLDQYAKSIGLAFQVQDDIL  239
YP_002796315.1    ALDQTALEYMHCLKTGALIQAAVRLGALA-GSPDDDELA-ALDRYARRIGLAFQVIDDVL  227
NP_252732.1       ALDQAALEVMHRHKTGALIEASVRLGALASGRAEPASLA-ALERYAEAIGLAFQVQDDIL  225
YP_088252.1       QISLSELEQIHRNKTGALLSAALKMGFICSSHFADNALEAKLDRYAAAIGLAFQVQDDIL  230
NP_245470.1       HISLIELEQIHRNKTGAMLSAAIQLGRICSPHFKNDTLAQQLQRYSEAIGLAFQVQDDIL  225
                   :  **  :* ****:: * *::::*    :.        *  *: *:  ******  **:*

IspA_E.coli       DVVGDTATLGKRQGADQQLGKSTYPALLGLEQARKKARDLIDDARQSLKQLAEQS---LD  283
YP_215451.1       DVVGDTATLGKRQGADQQLGKSTYPALLGLEQARNKARDLIEDARQSLHQLAAQS---LD  283
YP_003209360.1    DVVGDTATLGKRQGADQQLGKSTYPALLGLEQAQAKARSLCDDALAALAPLKAQA---LD  283
YP_049238.1       DVVGDSATTGKRQGADQQLGKSTYPSLLGLDNARKKAQELYQESLASLDDLVASSPIPLN  287
YP_002924367.1    DEIGEARKTGKKPKSDQQRGKATYPGLLSLKGAQKKMAALYQSSLSALTVPEASV---YN  296
YP_002796315.1    DCEADSATLGKTAGKDAAHDKPTYVSLMGLGEARSYAHALLADAHEALALFGARA-----  282
NP_252732.1       DVESDTATLGKTQGKDQAHNKPTYPALLGLEAAKGYALELRDLALAALDGFPPSA-----  280
YP_088252.1       DIEGDLAAIGKNVGSDLESDKSTYPKLLGLAGAKQKARELYVAAVGELEHLPFDT-----  285
NP_245470.1       DIEGESDIIGKTVGSDLLADKSTYPKLLGLAGAKQKAQELYQNAIAELESIPFDT-----  280
                  * .:     **    *    .*.**  *:.*   *:        *    :  *

IspA_E.coli       TSALEALADYIIQRNK  299
YP_215451.1       TSALEALANYIIQRDK  299
YP_003209360.1    TATLEALANFIIQRDK  299
YP_049238.1       IAPLQALANFIVERDK  303
YP_002924367.1    TLPLQACAHFILERHY  312
YP_002796315.1    -RRLQQLADYIVARSF  297
NP_252732.1       -DPLRQLARYIVERRN  295
YP_088252.1       -TALRALAEFIINRKN  300
NP_245470.1       -SALRAIAEFVVNRKS  295
                    *.  *  * ::: *
```

```
ispA      ---------MDFPQQLEACVKQANQALSRFIAPLP----FQNTPVVETMQYGALLGGKRL
ERG20     MASEKEIRRERFLNVFPKLVEELNASLLAYGMPKEACDWYAHSLNYNTPGGKLNRGLSVV
                   * : :    *:: * :*   : *         : ::    :*      *  . :

ispA      RPFLVYATGHMFGVSTNTLDAPAAAVECIHAYSLIHDDLPAMDDDDLRRGLPTCHVKFGE
ERG20     DTYAILSNKTVEQLGQEEYEKVAILGWCIELLQAYFLVADDMMDKSITRRGQPCWYKVPE
           .: : :.   :  :.  :   *    **.  .  .    * *..: *    .* *. * ispA      ANAILAGDALQTLAFSILSDADMPEVSDRDRISMISELASASGIAGMCGGQALDLDAEGK
ERG20     VGEIAINDAFMLEAA--IYKLLKSHFRNEKYYIDITELFHEVTFQTELG-QLMDLITAPE
           .. *  .**:   *    :    ... :..    *:**     :    * * :**  :  :

ispA      HVPLDALERIHRHKTGALIRAAVR-------LGALSAGDKGRRALPVLDKYAESIGLAFQ
ERG20     DKVDLSKFSLKKHSFIVTFKTAYYSFYLPVALAMYVAGITDEKDLKQARDVLIPLGEYFQ
                :   :::*.  . :::*         *.   ** ...: *     .  .:*  ** ispA      VQDDILDVVGDTATLGKRQGADQQLGKSTYPALLGLEQARKKARDLIDDARQSLKQLAEQ
ERG20     IQDDYLDCFGTPEQIG-KIGTDIQDNKCSWVINKALELASAEQRKTLDENYGKKDSVAEA
          :*** ** .*  .    :*  : *:* * .*.::       .** *  :    .*:     . ..:**

ispA      S---------------LDTSALEALADYIIQRNK--------------------
ERG20     KCKKIFNDLKIEQLYHEYEESIAKDLKAKISQVDESRGFKADVLTAFLNKVYKRSK
                         :  *  : *    * *  ::
```

Figure 7

PRODUCTION OF GERANYL DIPHOSPHATE

CROSS-REFERENCES TO RELATED APPLICATIONS

This application claims the benefit of U.S. Provisional Application Nos. 61/319,586 and 61/319,560 filed Mar. 31, 2010, which are incorporated herein by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX 3- 044US1_ST 25.TXT, created on Aug. 7, 2012, 31,780 bytes, machine format IBM-PC, MS-Windows operating system, is hereby incorporated by reference.

FIELD OF THE INVENTION

The invention relates to recombinant geranyl diphosphate synthases. The invention also relates to genes, vectors, host cells, and expression systems to produce geranyl diphosphate and/or monoterpenes.

BACKGROUND OF THE INVENTION

Terpenes are hydrocarbons commonly produced by a wide variety of plants but also found in many other organisms, including bacteria, fungi, algae, insects, and some larger animals. Terpenes are assembled by a terpene synthase from five-carbon building blocks called isoprenes ($C_5H_8$) that can be joined end-to-end in linear chains or can be arranged to form rings.

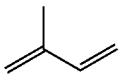 isoprene ($CH_2 = C(CH_3)CH = CH_2$)

Terpenes are useful in many commercial applications, including biofuels, solvents, pharmaceuticals, cosmetics, fragrances, essential oils, resins, pigments and colorants, antimicrobial and anti-fungal agents, flavorings, nutraceuticals, and medicaments. Although terpenes can be extracted from natural sources, extraction is problematic for commercial applications due to low yields, difficulties in large-scale cultivation of the natural sources, and, in some cases, toxicity of the solvents required for extraction. Chemical synthesis of terpenes is also difficult and costly. Thus, there is a need for alternative sources of terpenes, including ways to manufacture them on a commercial scale. Reports describe microbial strains that have been engineered to produce terpenes. See Martin et al., (2003) *Nature Biotech.* 21:796-802; U.S. Pat. No. 6,818,424; Yuba et al. (1996) Arch Biochem Biophys 332:280-287 (reporting limonene synthase from *Perilla frutescens* expressed in *E. coli*)).

Certain plants and microorganisms use geranyl diphosphate ("GPP") as a ten-carbon phosphorylated terpene precursor. In one biosynthetic pathway, GPP is produced from the five-carbon precursors isopentenyl pyrophosphate (IPP) and dimethylallyl pyrophosphate (DMAPP). Prenyl transferases (e.g., GPP synthases) are described in, e.g., Schmidt & Gershenzon, *Phytochemistry* 69:49-57 (2008); Bouvier et al., *The Plant Journal* 24(2):241-252 (2000); Burke & Croteau, *Archives of Biochemistry and Biophysics* 405:130-136 (2002); Burke et al, *PNAS,* 96(23):13062-13067 (1999); U.S. Pat. No. 6,303,330; Vandermoten et al, *FEBS Letters* 582:1928-1934 (2008).

GPP can combine with IPP to make the fifteen-carbon phosphorylated terpene precursor farnesyl diphosphate (FPP). Typically, both steps in this scheme—IPP/DMAPP to GPP and GPP to FPP are facilitated by a single enzyme: an FPP synthase, such IspA from *E. coli*.

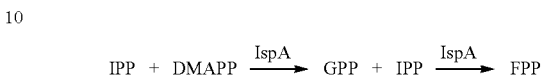

Because IspA preferentially produces FPP (C15) compared to GPP (C10), this pathway likewise leads to preferential production of terpenes having fifteen or more carbon atoms rather than monoterpenes having only ten carbon atoms.

BRIEF SUMMARY OF THE INVENTION

The invention provides recombinant geranyl diphosphate (GPP) synthases exhibiting improved properties, especially improved GPP production and/or improved GPP selectivity.

In one aspect, a recombinant geranyl diphosphate (GPP) synthase comprising a polypeptide sequence having at least 50% sequence identity to SEQ ID NO: 2, and having an amino acid substitution corresponding to at least one of positions M154 and Q158 of SEQ. ID NO: 2.

In one aspect, the recombinant GPP synthase comprises a polypeptide sequence having at least 90%, 95%, or 99% sequence identity to SEQ ID NO: 2, and having an amino acid substitution at position M154 and/or Q158.

In one aspect, the GPP synthase further comprises the amino acid substitution S80F.

In one aspect, the amino acid at position M154 is histidine, tyrosine, phenylalanine, tryptophan, or arginine. In one aspect, it is histidine, tyrosine, or tryptophan.

In another aspect, the amino acid at position Q158 is methionine, phenylalanine, leucine, or tryptophan.

In another aspect, the GPP synthase also has a substitution at position L112. In one aspect, the amino acid at position 112 is histidine, tyrosine, phenylalanine, tryptophan, or arginine. In one aspect, it is histidine or tyrosine.

In one aspect, the GPP synthase also has an amino acid substitution at one or more of positions V32, A54, I76, P99, R136, I139, A159, L162, G201, K237, A241, and L290. In one aspect, the synthase includes at least one of: V32A, A54V, I76V, P99S, R136C, I139V, A159M, A159S, L162M, G201Q, K237N, A241V, and L290P. In one aspect, the synthase has an amino acid substitution at position A159 and/or L162.

In one aspect, the GPP synthase is one of the variants listed in Table 3.

In one aspect, the GPP synthase exhibits improved GPP synthase activity, e.g., improved GPP selectivity, compared to SEQ ID NO: 2 or SEQ ID NO: 3 when expressed in *E. coli* under the same culture conditions.

In other aspects, the invention provides polynucleotides encoding the above described GPP synthases, and vectors and host cells (e.g., *E. coli*) comprising the polynucleotides.

In another aspect, the invention provides a method of producing GPP in a host cell by inducing a host cell (e.g., *E. coli*) to express a GPP synthase as described, and culturing the host cell under conditions in which the GPP synthase acts on IPP and DMAPP to produce GPP. The method can further include introducing a vector comprising the GPP synthase gene into the host cell.

In another aspect, the method can further include reacting the GPP with a monoterpene synthase (e.g., a cyclic monoterpene synthase) to produce monoterpenes. The method can also include recovering the monoterpenes.

BRIEF DESCRIPTION OF THE DRAWINGS

FIG. 2 (A) depicts the wild-type (WT) polynucleotide (SEQ ID NO: 1); (B) the WT amino acid sequence (SEQ ID NO: 2) of IspA isolated from E. coli, and (C) the amino acid sequence of the S80F variant of WT IspA (SEQ ID NO: 3). In SEQ ID NO: 2, the position corresponding to variant S80F is in bold and underlined.

FIG. 5 illustrates and an amino acid alignment of wild-type E. coli IspA (SEQ ID NO: 2) with Avian FPP Synthase (SEQ ID NO: 6).

FIG. 6 illustrates an alignment of wild-type IspA from E. coli (SEQ ID NO: 2) with other prenyl transferase enzymes wherein YP_215451.1, Salmonela enterica has SEQ ID NO: 7; YP_003209360.1, Cronobacter turicensis has SEQ ID NO: 8; YP_049238.1, Pectobacterium astrosepticum has SEQ ID NO: 9; YP_002924367.1, Candidatus hamiltnella has SEQ ID NO: 10; YP_002796315.1, Laribacter hongkongensis has SEQ ID NO: 11; NP_252732.1, Pseudomonas aeruginosa has SEQ ID NO: 12; YP_088252.1, Mannheimia succiniciproducens has SEQ ID NO: 13; and Patuerella multocida, NP_245470.1 has SEQ ID NO:14. The alignment was carried out using the Needleman-Wunsch procedure with blosum62 as the substitution matrix. A Gap start penalty of 7 and gap extend penalty of 1 was used. A tree-based strategy was used for the initial pair wise build-up.

FIG. 7 illustrates an alignment of wild-type IspA from E. coli (SEQ ID NO: 2) with ERG20 (CAA89462.1), an FPP synthase from Saccharomyces cerevisiae. The sequence alignment was performed according to the same method as FIG. 6.

DETAILED DESCRIPTION OF THE INVENTION

I. Introduction

Figure 1:
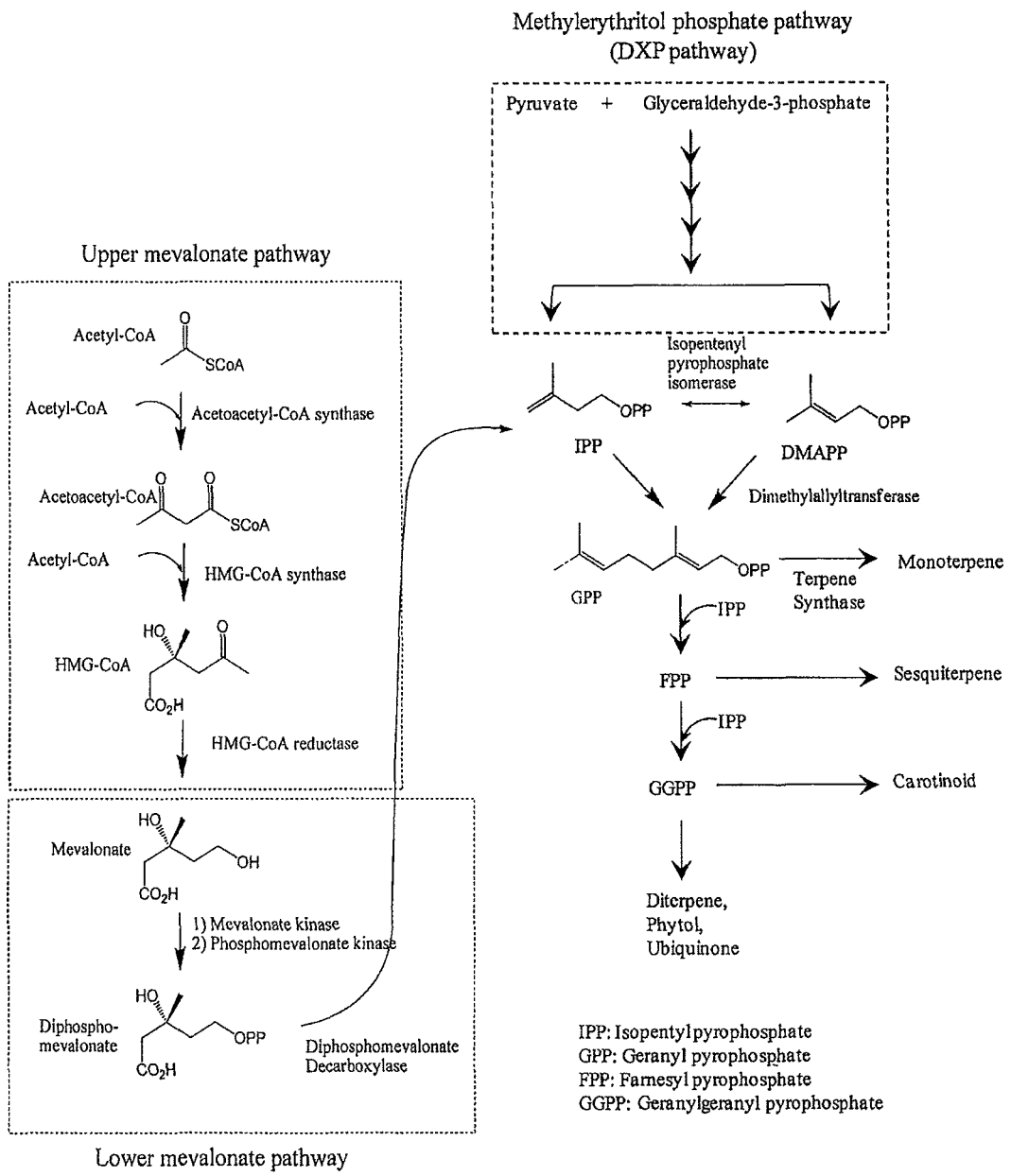
FIG. 1 generally illustrates the mevalonate and DXP pathway wherein IPP and DMAPP are produced and then reacted to produce GPP. GPP can then be modified to produce monoterpenes, e.g., sabinene, or it can be reacted with IPP to produce FPP leading to the production of sesquiterpenes. Further reactions with IPP will lead to other diphosphate intermediates and to longer-chain terpenes.

This invention provides recombinant prenyl transferases that are useful for producing GPP, and thus, in turn, may be useful for producing monoterpenes. Because the recombinant synthases exhibited improved GPP production and/or improved GPP selectivity, they are referred to herein as GPP synthases. Preferably, the recombinant GPP synthase is derived from an FPP synthase, such as IspA from E. coli. The present invention identifies novel mutations that influence chain-length specificity and improve pathway flux and selectivity for GPP production.

In another embodiment, this disclosure provides genes encoding the recombinant GPP synthases, vectors including such genes, and host cells capable of expressing such genes. In one embodiment, the present invention includes methods for producing GPP by culturing host cells (e.g., E. coli) that express a gene (e.g., a heterologous gene) encoding a recombinant GPP synthase. By co-expressing a terpene synthase, which converts GPP to a terpene, such cells may be used for the commercial production of monoterpenes.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references. For example, standard methods are described by Sambrook et al. Molecular Cloning: A Laboratory Manual, 2d ed. (1989) Cold Spring Harbor Laboratory Press, Cold Spring Harbor, N.Y.; Silhavy, et al. Experiments with Gene Fusions. (1984) Cold Spring Harbor Laboratory Cold Press Spring Harbor, N.Y.; Ausubel, et al., Current Protocols in Molecular Biology. (1987) Greene Publishing Assoc. and Wiley-Interscience.

The following abbreviations are used herein: IPP means isopentenyl pyrophosphate or isopentenyl diphosphate; GPP means geranyl pyrophosphate or geranyl diphosphate; FPP means farnesyl diphosphate; DMAPP means dimethylallyl pyrophosphate; DXP means deoxyxylulose phosphate; MEP means 2-methyl-D-erythritol-4-phosphate; DXP pathway and MEP pathway refer to the non-mevalonate pathway or mevalonate-independent pathway; and HMG-CoA means 3-hydroxy-3-methylglutaryl-CoA.

The term "isoprenoid" or "terpenoid" refers to any compound comprising one or more five-carbon isoprene building blocks, including linear and cyclic terpenoids. As used herein, the term "terpene" is interchangeable with terpenoid and isoprenoid. When terpenes are modified chemically, such as by oxidation or rearrangement of the carbon chain, the resulting compounds are generally referred to as terpenoids, also called isoprenoids.

Terpenoids can be named according to the number of carbon atoms present, using groups of 5 and 10 carbons as a reference. For example a hemiterpenoid (C5) has one isoprene unit (a half-terpenoid); a monoterpenoid (C10) has two isoprene units (one terpenoid); a sesquiterpenoid (C15) has three isoprene units (1.5 terpenoids); and a diterpenoid (C20) has four isoprene units (or two terpenoids). Typically, a monoterpenoid is produced in nature from the C10 terpenoid precursor geranyl pyrophosphate (GPP). Similarly, a "cyclic monoterpene" refers to a cyclic or aromatic terpenoid (i.e., comprising a ring structure). It is made from two isoprene building blocks, typically from GPP. Linear monoterpenes include but are not limited to geraniol, linalool, ocimene, and myrcene. Cyclic monoterpenes (monocyclic, bicyclic and tricyclic) include, but are not limited to, limonene, pinene, carene, terpineol, terpinolene, phellandrene, thujene, tricyclene, borneol, sabinene, and camphene.

A "terpenoid synthase" refers to an enzyme capable of catalyzing the conversion of one terpenoid or terpenoid precursor to another terpenoid or terpenoid precursor. For example, a GPP synthase is an enzyme that catalyzes the formation of GPP, e.g. from the terpenoid precursors IPP and DMAPP. Similarly, an FPP synthase is an enzyme that catalyzes the production of FPP, e.g. from GPP and IPP. Terpene synthases are enzymes that catalyze the conversion of a prenyl diphosphate (such as GPP) into an isoprenoid or an isoprenoid precursor. The term includes both linear and cyclic terpene synthases.

A "cyclic terpenoid synthase" refers to an enzyme capable of catalyzing a reaction that modifies a terpenoid or terpenoid precursor to provide a ring structure. For example, a cyclic monoterpenoid synthase refers to an enzyme capable of using a linear monoterpene as a substrate to produce a cyclic or aromatic (ring-containing) monoterpenoid compound. One example would be sabinene synthase, which is capable of catalyzing the formation of the cyclic monoterpene sabinene from the linear monoterpene precursor GPP. As used herein, the term "terpene synthase" is interchangeable with terpenoid synthase.

A prenyl transferase or isoprenyl transferase enzyme, also called a prenyl or isoprenyl synthase is an enzyme capable of catalyzing the production of a pyrophosphate precursor of a terpenoid or isoprenoid compound. The term "IspA" is a prenyl transferase or isoprenyl transferase enzyme that is encoded by DNA or RNA corresponding to or derived from an IspA gene and is capable of catalyzing the formation of geranyl diphosphate (GPP) or farnesyl diphosphate (FPP) in the presence of a suitable substrate.

The "terpene pathway" refers to the cellular metabolic pathway present in organisms (e.g., eukaryotes and bacteria such as *E. coli*) involved in the production of terpenes and terpenoids. As used herein, the term "terpene pathway" is interchangeable with mevalonate pathway, HMG-CoA reductase pathway, mevalonate-dependent pathway, isoprenoid pathway, lower mevalonate pathway and non-mevalonate pathway (e.g., DXP pathway).

The terms "culturing" and "cultivation" refer to growing a population of microbial cells under suitable conditions in a liquid or solid medium. In some embodiments, culturing refers to growing a recombinant host cell comprising a polynucleotide encoding a variant geranyl diphosphate synthase according to the invention.

A "gene" refers to a nucleic acid fragment comprising DNA and/or RNA that is capable of being expressed as a specific protein, with or without regulatory sequences before the coding sequence (5' non-coding sequences) and regulatory sequences after the coding sequence (3' non-coding sequences). A "native" or "wild-type" gene refers to a gene as found in nature. "Endogenous gene" refers to a native gene, including its native regulatory sequences, e.g. as found in its natural location in the genome of an organism.

A modified gene, also called a variant, mutant, evolved, or altered gene, refers to a gene having a coding sequence or regulatory sequence that is changed from the coding sequence or regulatory sequence of a reference or "parent" gene, such as a native gene. Typically, though not necessarily, a modified gene indicates a change in the coding sequence, whether or not a regulatory sequence is also changed. A "chimeric gene" refers to any gene comprising regulatory and coding sequences that are not found together in nature. A chimeric gene may comprise regulatory sequences and coding sequences that are derived from different (i.e. heterologous) sources, or regulatory sequences and coding sequences derived from the same source (homologous), but arranged in a manner different than is found in nature. A "foreign" or "heterologous" gene refers to a gene not normally found in the host organism, but that is introduced into the host organism, e.g. recombinant methods of gene transfer. Foreign genes can comprise native genes inserted into a non-native organism, modified genes, or chimeric genes.

DNA and RNA have their ordinary meaning. Deoxyribonucleic acid (DNA) is a nucleic acid that contains genetic instructions and comprises a chain or sequence of nucleotides or bases, adenine (A), thymine (T), cytosine (C) and guanine (G), on a backbone of deoxyribose sugars. DNA may be double-stranded or single stranded. It is the sequence of these four bases along the backbone that encodes genetic information. This information is read using the genetic code, which specifies the sequence of the amino acids within proteins. The code is read by copying stretches of DNA into the related nucleic acid RNA, in a process called transcription. Ribonucleic acid (RNA) is a nucleic acid that contains genetic instructions and comprises a chain or sequence of nucleotides or bases, adenine (A), uracil (U), cytosine (C) and guanine (G), on a backbone of ribose sugars.

Complementary DNA (cDNA) is DNA synthesized from an mRNA template in a reaction catalyzed by the enzyme reverse transcriptase. cDNA is often used to clone genes, i.e., to express a specific protein or enzyme in a cell that does not normally express that protein (heterologous expression). cDNA that codes for the protein or enzyme is transferred to the recipient cell, also called a host cell. Messenger ribonucleic acid (mRNA) is a molecule of RNA that encodes for a protein product. Messenger RNA is transcribed from a DNA template and carries coding information to the cell ribosomes for protein synthesis. Using the genetic code, where each of the 20 native amino acids is represented by one or more combination of nucleic acid triplets, the mRNA is translated into a polymer of amino acids: a protein or enzyme.

"Coding sequence" refers to a nucleic acid sequence (DNA and/or RNA) that codes for the expression of a specific amino acid sequence.

A "regulatory sequence" refers to nucleotide sequences located upstream (5' non-coding sequences), within, or downstream (3' non-coding sequences) of a coding sequence that influence the transcription, RNA processing or stability, or translation of an associated coding sequence. Regulatory sequences include, but are not limited to, promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. Typically a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." An "inducible promoter" is one that causes a gene to be expressed under specific conditions.

The term "operably linked" refers to the association of any two nucleic acid sequences in a construct such that the function of one of the two sequences is affected by the other sequence. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

An "operon" is a functional nucleic acid construct comprising regulatory sequences including at least a promoter, and one or more genes, which is controlled as a unit to produce RNA, typically messenger RNA (mRNA), in the process of transcription. The "origin of replication" is a particular sequence in a genome at which replication is initiated.

The term "expression" refers to the production of an amino acid or polypeptide product encoded by a coding sequence, i.e. as a consequence of transcribing coding DNA to corresponding RNA and translating the RNA into a polypeptide or a sequence of amino acid residues.

"Transformation" refers to the stable transfer of a nucleic acid construct into the genome of a host organism. Such constructs typically comprise one or more genes, e.g. coding sequences with or without regulatory sequences, although typically if not necessarily at least a coding sequence and promoter are provided. Host cells or organisms containing the transferred nucleic acid construct are referred to as "transgenic," "recombinant" or "transformed" cell or organisms. A nucleic acid construct can be provided for example as a "plasmid", "vector" or "cassette" as known in the art. Such elements may be autonomously replicating sequences, genome integrating sequences, phage or nucleotide sequences, linear or circular, of a single- or double-stranded DNA or RNA, and derived from any source. Typically a number of nucleotide sequences have been joined or recombined into a unique construction that is capable of introducing a promoter and coding sequence for a selected gene product into a cell. A "transformation construct," including a "transformation" cassette, vector or plasmid, refers to a construct containing a foreign gene and having additional elements that facilitate transformation of a particular host cell. "Expression construct," including an "expression" cassette, vector or plasmid, refers to a construct containing a foreign gene and having additional elements that allow for expression of that gene in a foreign host.

Amino acids, amino acid residues, and amino acid sequences each have their ordinary meaning, and each amino acid residue can be represented using conventional one-letter and/or three-letter abbreviations. Altering an amino acid sequence means making a change to one or more amino acids or residues of a sequence, including addition, deletion, and/or substitution.

Except as otherwise noted, the terms "percent identity," "% identity," "percent identical," and "% identical" are used interchangeably herein to refer to the percent amino acid sequence identity that is determined, using any suitable method known in the art. "Percent identity" in the context of two or more polypeptide sequences, refers to two or more sequences or subsequences that are the same or have a specified percentage of amino acid residues that are the same (i.e., share at least about 50% identity, for example, at least about 60%, 70%, 80%, 85%, 88%, 89%, 90%, 91%, 92%, 93%, 94%, 95%, 96%, 97%, 98%, 99% identity over a specified region to a reference sequence), when compared and aligned for maximum correspondence over a comparison window, or designated region as measured using a sequence comparison algorithms or by manual alignment and visual inspection. Sequences that are at least about 88%, 89%, 90%, 91%, 92%, 93%, 94%, 95%, 96%, 97%, 98%, 99% identical can be called "substantially identical" or having "substantial sequence identity."

Two polynucleotide or amino acid sequences may be aligned manually (i.e., by inspection). Manual alignment is particularly convenient for aligning pairs of similar (e.g., 70% or more sequence identity) polypeptide sequences. While optimal alignment and scoring can be accomplished manually, the process is facilitated by the use of a computer-implemented alignment algorithm. Sequence comparison algorithms are well known in the art. One example is the Needleman-Wunsch procedure, *J. Mol. Biol.* 48: 443-453 (1970), with blosum62 as the substitution matrix. A Gap start penalty of 7 and gap extend penalty of 1 can be used. A tree-based strategy can be used for the initial pairwise build-up. Another example is BLAST, available over the world wide web (see, e.g., Altschul et al., 1990, *J. Mol. Biol.* 215: 403-10) and, e.g., gapped BLAST 2.0 (see Altschul, et al. 1997, *Nucleic Acids Res.*, 25:3389-3402) made available to the public at the National Center for Biotechnology Information Website. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For amino acid sequences, a scoring matrix is used to calculate the cumulative score. For amino acid sequences, the BLASTP program uses as defaults a word size (W) of 3, an expectation (E) of 10, and the BLOSUM62 scoring matrix (see Henikoff & Henikoff, 1989, *Proc. Natl. Acad. Sci. USA* 89:10915, incorporated herein by reference). Two sequences may be optimally aligned when they are aligned for similarity scoring using a defined amino acid substitution matrix (e.g., BLOSUM62), gap existence penalty and gap extension penalty so as to arrive at the highest score possible for that pair of sequences. The alignment is defined by the amino acid position of each sequence at which the alignment begins and ends, and optionally by the insertion of a gap or multiple gaps in one or both sequences so as to arrive at the highest possible score. Amino acid substitution matrices and their use in quantifying the similarity between two sequences are well-known in the art. The gap existence penalty is imposed for the introduction of a single amino acid gap in one of the aligned sequences, and the gap extension penalty is imposed for each additional empty amino acid position inserted into an already opened gap.

The term "improved GPP production" means that the recombinant GPP synthase produces more GPP compared to a wild-type or reference prenyl transferase. Improved GPP production can be assessed, for example by expressing the recombinant GPP synthase and the wild-type or reference prenyl transferase in a host cell and measuring the relative amounts of GPP produced. For example, GPP production in *E. coli* expressing the recombinant GPP synthase can be compared to GPP production by *E. coli* (under the same culture conditions) expressing the wild-type or reference prenyl transferase (e.g., an endogenous prenyl transferase). GPP production can be measured directly or indirectly by using a reporter system (e.g., a terpene reporter). Exemplary expression and assay methods are described in Example 2. Improved GPP production can be achieved by higher selectivity, higher specific activity, higher rate of reaction, or higher yield of GPP relative to FPP in comparison to a wild-type or reference prenyl transferase under the same conditions. The reference prenyl transferase can be a known FPP synthase, a known *E. coli* FPP synthase, IspA enzyme (SEQ ID NO: 2), or *E. coli* IspAS80F enzyme (SEQ ID NO: 3). Improved GPP production can also lead to improved monoterpene production because increased production of GPP leads to increased production of monoterpenes when cells are cultured to co-express a monoterpene synthase. The recombinant GPP synthases may also exhibit other improved properties, e.g. a longer half-life, higher stability, etc. Improved GPP production includes improved GPP selectivity.

"Improved GPP selectivity" means that the product ratio GPP:FPP is higher for the recombinant GPP synthase compared to a wild-type or reference prenyl transferase. Improved GPP selectivity can be measured similarly to the assays described above for improved GPP production when, in addition to measuring GPP or a GPP reporter system (e.g., a monoterpene), one also measures FPP or an FPP reporter system (e.g., a terpene having more than 10 carbons). In some cases, improved GPP selectivity means that the GPP synthase produces more GPP than FPP.

The term "biosynthetic pathway" is used to refer to the series of enzymes and steps in a pathway leading to the biosynthesis of a molecule.

As used herein the term "isolated" is meant to describe a polynucleotide, a polypeptide, an enzyme, a compound produced by a cell or a cell that is in an environment different from that in which the polynucleotide, the polypeptide, the enzyme, compound or the cell naturally occurs and includes a polynucleotide, a polypeptide, an enzyme, compound or a cell once removed from the environment in which it naturally occurs.

A nucleic acid (such as a polynucleotide), a polypeptide, or a cell is "recombinant" when it is artificial or engineered, or derived from or contains an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

The term "host cell" as used herein denotes a eukaryotic cell or a prokaryotic cell containing a recombinant polynucleotide and includes the progeny thereof. In one specific embodiment, a transformed host cell includes a cell that has been transformed with a polynucleotide encoding a prenyl transferase according to the invention. While one skilled in the art is aware of many type of cells that could be used as host cells, some examples include but are not limited to bacterial cells, such as *Bacillus* sp. and *E. coli*.

III. Genetic Engineering of a Prenyl Transferase

To make the recombinant GPP synthase of the present invention, one or more wild-type or variant prenyl transferase amino acid sequences were identified as reference sequences. Suitable prenyl transferases are those that produce both GPP and FPP, including those that predominantly produce FPP. In one embodiment, wild-type *E. coli* IspA (SEQ ID NO: 2) is the reference sequence. In another embodiment, the reference sequence is a variant of a wild-type prenyl transferase (e.g., IspA) sequence, such as SEQ ID NO: 3. Accordingly, the methods of genetic engineering are described below with reference to the IspA sequence (e.g., the wild-type and/or variant IspA sequence).

Next, certain targeted regions (e.g., regions in or around the active site) of IspA were identified for alteration. X-ray crystallography studies of avian FPP synthase revealed the IspA enzyme is a homodimer, and the subunits each contain a single site for C5 to C15 elongation. Tarshis et al., *Proc. Natl. Acad. Sci. USA* 90:15018-15023 (1996). The putative catalytic site consists of a large central cavity formed by a bundle of 10 alpha-helices. Id. Two aspartate-rich motifs with the sequence DDXXD are located on opposite walls of this cavity. The DDXXD sequences are highly conserved among prenyl transferases, and are essential for catalytic efficiency. See also, Nakane et al., EP 0 821 065; and Ohto et al., U.S. patent application No. 2001/0051359. The two aspartate-rich motifs are referred to as first and second aspartate-rich motifs (FARM and SARM), respectively. Wang and Ohnuma (2000). IspA from *E. coli* is understood to have a similar structure and function.

Genetic engineering methods were used to produce iterative combinations of alterations at the selected sites. Structural analysis of IspA was used to design saturation mutagenesis and semi-synthetic DNA shuffling libraries. Methods for generating variant libraries are well known in the art. For example, mutagenesis and genetic engineering methods can be readily applied to polynucleotides or the polynucleotides of the present invention (described below) to generate variant libraries that can be expressed, screened, and assayed using the methods described herein. Mutagenesis and directed evolution methods are well known in the art. See, e.g., Ling, et al., *Anal. Biochem.*, 254(2):157-78 (1997); Dale, et al., *Methods Mol. Biol.*, 57:369-74 (1996); Smith, *Ann. Rev. Genet.*, 19:423-462 (1985); Botstein, et al., *Science*, 229:1193-1201 (1985); Carter, *Biochem. J.*, 237:1-7 (1986); Kramer, et al., *Cell*, 38:879-887 (1984); Wells, et al., *Gene*, 34:315-323 (1985); Minshull, et al., *Current Opinion in Chemical Biology*, 3:284-290 (1999); Christians, et al., *Nature Biotechnology*, 17:259-264 (1999); Crameri, et al., *Nature*, 391:288-291; Crameri, et al., *Nature Biotechnology*, 15:436-438 (1997); Zhang, et al., *Proceedings of the National Academy of Sciences, U.S.A.*, 94:45-4-4509; Crameri, et al., *Nature Biotechnology*, 14:315-319 (1996); Stemmer, *Nature*, 370:389-391 (1994); Stemmer, *Proceedings of the National Academy of Sciences, U.S.A.*, 91:10747-10751 (1994); WO 95/22625; WO 97/0078; WO 97/35966; WO 98/27230; WO 00/42651; and WO 01/75767, all of which are incorporated herein by reference. Further methods for identifying candidates for amino acid alteration of an enzyme are known. These methods include both computational and rational engineering methods. See for example: Arnold F H. *Nature* 409(6817): 253-7 (2001); Meyer M M, et al., *Protein Eng Des Sel.* 19(12):563-70 (2006); Chica R A, et al., *Curr Opin Biotechnol.* 16(4):378-84 (2005); Diaz N, et al., *Proteins* 78(1):1-11 (2010); Ortiz A R, et al., *Curr Top Med. Chem.* 6(1):41-55 (2006); Damborsky J, and Brezovsky J. *Curr Opin Chem. Biol.* February; 13(1):26-34 (2009); Lippow S M and Tidor B. *Curr Opin Biotechnol.* 18(4):305-11 (2007). Reference is also made to the methods described in U.S. Pat. No. 6,117, 679 (Stemmer); U.S. Pat. No. 6,376,246 (Crameri et al.); U.S. Pat. No. 6,586,182 (Patten et al.); US Pat. Appln No. 20080220990A1 (Fox) and U.S. Pat. Appln. No. 20090312196A1 (Colbeck et al.).

In some embodiments, a recombinant GPP synthase comprises a polypeptide sequence that has at least 50%, 80%, 90%, 95%, or 99% sequence identity to a prenyl transferase selected from: wild-type IspA SEQ ID NO:2, variant IspA SEQ ID NO:3, any one of the variants described in Table 3, and any one of the prenyl transferases described in FIG. 6. In some embodiments, a recombinant GPP synthase comprises a polypeptide sequence that is substantially identical (e.g., at least 90%, 95%, or 99%) to SEQ ID NO:2, SEQ ID NO:3, or any of the variants listed in Table 3. In one embodiment, the recombinant GPP synthase comprises a polypeptide sequence that is substantially identical to SEQ ID NO:2. In another embodiment, the recombinant GPP synthase comprises a polypeptide sequence that is substantially identical to SEQ ID NO:3. In one embodiment, the sequence identity is at least 90%. In another embodiment, the sequence identity is at least 95%. In yet another embodiment, the sequence identity is at least 99%.

The recombinant GPP synthase polypeptide also comprises an amino acid substitution at one or more of the positions described below. The mutation positions are identified according to SEQ ID NO:2, but corresponding positions in other homologs can be determined by sequence alignment techniques known in the art.

In one embodiment, the recombinant GPP synthase comprises a polypeptide sequence having at least 90% sequence identity to SEQ. ID NO: 2, and having an amino acid substitution at one or more of positions L112, M154, Q158, A159, and A241 of SEQ. ID NO. 2. In some embodiments, the recombinant GPP synthase has an amino acid substitution at one or more of positions L112, M154, and Q158. In some embodiments, the recombinant GPP synthase has an amino acid substitution at one or both of positions M154 and Q158.

In some embodiments, the amino acid at position M154 is histidine (H), tyrosine (Y), phenylalanine (F), tryptophan (W), or arginine (R). In some embodiments, the amino acid at position M154 is histidine (H), tyrosine (Y), or tryptophan (W).

In some embodiments, the amino acid at position Q158 is methionine (M), phenylalanine (F), leucine (L), or tryptophan (W).

In another embodiment, the GPP synthase has an amino acid substitution at position L112 of SEQ ID NO:2. In some embodiments, the amino acid at position L112 is histidine (H), tyrosine (Y), phenylalanine (F), tryptophan (W), or arginine (R). In some embodiments, the amino acid as position 0L112 is histidine (H), tyrosine (Y), phenylalanine (F), or arginine (R). In some embodiments, the amino acid at position L112 is histidine (H) or tyrosine (Y).

In some embodiments, the GPP synthase has an amino acid substitution at position S80. In one embodiment, the substitution is S80F.

In one embodiment, the recombinant GPP synthase has at least two amino acid substitutions. In one embodiment, one of the substitutions is at position L112. In one embodiment, the recombinant GPP synthase has a first substitution at position L112, and a second substitution at position M154 or Q158. In one embodiment, the recombinant GPP synthase as a substitution at positions 112 and 158. The substitutions at positions L112, M154, and/or Q158 can be those described above.

In other embodiments, the recombinant GPP synthase comprises a polypeptide sequence having at least 90% sequence identity to SEQ. ID NO. 2, and having an amino acid substitution at one or more of positions L112, M154, and Q158, and further having an amino acid substitution at one or more of positions V32, A54, I76, P99, R136, I139, A159, L162, G201, K237, A241, and L290. In some embodiments, the latter substitution is selected from: at position 32 is alanine (A), at position 54 is valine (V), at position 76 is valine (V), at position 99 is serine (S), at position 136 is cysteine (C), at position 139 is valine (V), at position 159 is methionine (M) or serine (S), at position 162 is methionine (M), at position 201 is glutamine (Q), at position 237 is asparagine N), at position 241 is valine (V), and at position 290 is proline (P).

In some embodiments, the substitutions are selected from L112H/Y/F and Q158M. In one embodiment, the recombinant GPP synthase comprises the substitutions L112F and Q158M and optionally at least one substitution selected from A159M, L162M, and L290P. In some embodiments, the recombinant GPP synthase comprises a polypeptide sequence having at least 90% sequence identity to SEQ. ID NO. 2, and having amino acid substitutions at positions L112, Q158, R136, I139, and A159. In some embodiments, the substitutions are L112H/Y/F/W/R, Q158M/F/L/W, R136C, I139V, and A159M.

In other embodiments, the recombinant GPP synthase is one of the variants listed in Table 3, or is substantially identical to SEQ ID NO: 2 and comprises the substitutions of one of the variants listed in Table 3.

Additional amino acid substitutions that may be useful in conjunction with those described herein, can be found in the literature. For example, the recombinant GPP synthase may also include amino acid substitutions corresponding to S82F of *Bacillus stearothermophilus* FPP synthase (Narita K et al., *J. Biochem.* 126:566-571 (1999)), S81F of SEQ ID NO:2 (Reiling K K et al., *Biotechnology and Bioengineering* 87(2): 200-212 (2004)), A116W and/or N144W of Avian FPP (Fernandez et al., *Biochemistry* 39:15316-15321 (2000)). See also Ohnuma et al., *J. Biol. Chem.* 271(3):18831-37 (1996) and Ohnuma et al., *J. Biol. Chem.* 271(17):10087-957 (1996).

Table 3 in Example 3 illustrates that *E. coli* IspA variant L112W increased the production of GPP. As demonstrated in FIG. 5, *E. coli* IspA residue L112, corresponds to the Avian FPP residue N144. Fernandez et al. (2000) demonstrated that a mutation at Avian FPP residue N144' to tryptophan also results in a terpene synthase that increases the production of GPP. Therefore, even though IspA and Avian's FPP synthase only share approximately 28% homology, a mutation at these aligned residues to tryptophan produces terpene synthases that selectively synthesize GPP. Accordingly, in other embodiments, the recombinant GPP synthase comprises a polypeptide sequence having at least 28% sequence identity to SEQ. ID NO. 2, and having an amino acid substitution corresponding to at least one of positions L112, M154, and Q158 of SEQ. ID NO. 2. In some embodiments, positions M154 and/or Q158 are substituted as described herein.

In some embodiments, the recombinant GPP synthase comprises a polypeptide having one or more conservative amino acid substitutions in addition to the specific substitutions described above. The term "conservative amino acid substitution" refers to the substitution of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; a group of amino acids having sulfur-containing side chains consists of cysteine and methionine and acidic side chains including glutamic acid and aspartic acid. Exemplary conservative amino acids substitution groups are:

valine-leucine-isoleucine, phenylalanine-tyrosine, lysine-arginine, alanine-valine, and asparagine-glutamine. In some embodiments, the recombinant GPP synthase will comprise no more than 10%, no more than 8%, no more than 5%, no more than 3%, no more than 2%, or no more than 1% of conservative amino acid substitutions. Therefore, in some embodiments, a recombinant GPP synthase comprises a polypeptide having at least 90% sequence identity to SEQ ID NO: 2 or SEQ ID NO: 3, having an amino acid substitutions corresponding to positions M154 and/or Q158 of SEQ ID NO: 2 or SEQ ID NO: 3, and having no more than 5% conservative substitutions compared to SEQ ID NO: 2 or SEQ ID NO: 3.

Other prenyl transferases, in particular those that produce both GPP and FPP in nature and those that predominantly produce FPP, can be mutated based on key regions in $E.\ coli$ IspA identified to be involved in GPP docking with $E.\ coli$ IspA. By targeting these docking regions, prenyl transferases can be produced that direct the terpene pathway flux towards GPP production and in turn result in higher monoterpene production as compared to wild-type prenyl transferases.

In some embodiments, a recombinant GPP synthase comprises an IspA homolog. An IspA homolog is an enzyme that has prenyl transferase activity (i.e., can convert IPP and/or DMAPP to GPP). Exemplary prenyl transferases FPP synthase and GPP synthase may include two aspartate-rich motifs referred to as first and second aspartate-rich motifs (FARM and SARM). The IspA homologs may be obtained, for example, from a bacterial, yeast, or plant source.

The wild-type IspA can be aligned with other prenyl transferase enzymes, as discussed above. Amino acid alterations in IspA variants having increased GPP production can be used as a basis for mutating a corresponding position in the prenyl transferase enzymes of FIG. 6, as well as others not listed here. An exemplary alignment is set forth in FIGS. 5 and 6. In the alignments, "*" indicates the identical amino acid in all sequences analyzed; ":" indicates conserved substitutions have been observed; and "." indicates semi-conserved substitutions are observed. The percent sequence identity of $E.\ coli$ IspA to each other enzyme in FIG. 6 is: (1) (YP_215451.1) $Salmonela\ enterica$ (89.7%); (2) (YP_049238.1) $Pectobacterium\ astrosepticum$ (72%); (3) (YP_003209360.1) $Cronobacter\ turicensis$ (77.7%); (4) (YP_002924967.1) $Candidatus\ hamiltnella$ (58.3%); (5) (YP_088252.1) $Mannheimia\ succiniciproducens$ (51%); (6) (YP_002796315.1) $Laribacter\ hongkongensis$ (49.3%); (7) $Patuerella\ multocida$ NP_245470.1 (49%); and (8) $Pseudomonas\ aeruginosa$ NP_252732.1 (49.3%). Similarly, the wild-type IspA was aligned with ERG20 (CAA89462.1), an FPP synthase from $Saccharomyces\ cerevisiae$ as shown in FIG. 7.

Mutations may be made in prenyl transferase enzymes, e.g. GPP and/or FPP synthases, based on mutations found in $E.\ coli$ IspA of the present invention. These variants may then be tested as described below in the Examples or a similar assay.

IV. Microbial Organisms for Producing GPP

A. Polynucleotides encoding GPP Synthase

In another embodiment, the invention provides polynucleotide sequences that code for the recombinant GPP synthases as described above. The polynucleotides may be operatively linked to one or more heterologous regulatory or control sequences that control gene expression to create a recombinant polynucleotide capable of expressing the polypeptide. Expression constructs containing a heterologous polynucleotide encoding the recombinant GPP synthase can be introduced into appropriate host cells.

Because of the knowledge of the codons corresponding to the various amino acids, availability of a polypeptide sequence provides a description of all the polynucleotides capable of encoding the subject polypeptide. The degeneracy of the genetic code, where the same amino acids are encoded by alternative or synonymous codons allows an extremely large number of nucleic acids to be made, all of which encode the recombinant GPP synthases disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein.

B. Vectors

Many embodiments of the invention utilize an expression vector that comprises a nucleotide sequence that encodes a recombinant GPS synthase as described above.

Suitable exemplary vectors include, but are not limited to, viral vectors (e.g., baculovirus vectors, bacteriophage vectors, and vectors based on vaccinia virus, poliovirus, adenovirus, adeno-associated virus, SV40, herpes simplex virus, and the like), phage, plasmids, phagemids, cosmids, phosmids, bacterial artificial chromosomes (BACs), bacteriophage PI, PI-based artificial chromosomes (PACs), yeast artificial chromosomes (YACs), yeast plasmids, and any other vectors suitable for a specific host cell (e.g., $E.\ coli$ or yeast).

Numerous suitable expression vectors are known to those of skill in the art, and many are commercially available. The following vectors are provided by way of example: for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector, with or without various improvements for expression, may be used so long as it is compatible with the host cell. In some embodiments, known $E.\ coli$ expression vectors would be suitable for transforming a bacterial cell host cell and particularly an $E.\ coli$ host with a vector comprising the polynucleotide.

Standard recombinant DNA techniques can be used to perform in vitro construction of plasmid and viral chromosomes, and transformation of such into host cells including clonal propagation.

The vector can include at least one origin of replication for the host cell into which the vector is to be introduced. If also necessary, the vector can include one or more copy-control sequences for controlling the number of copies of the vector in any one cell. By way of illustration, for use in $E.\ coli$ and other bacterial host cells, the vector preferably includes one or more bacterial origins of replication (Ori), and preferably ones that do not adversely affect gene expression in infected cells. For example, the bacterial Ori can be a pUC bacterial Ori relative (e.g., pUC, colEI, pSCIOI, pI 5A and the like). The bacterial origin of replication can also, for example, be a RK2 OriV or f 1 phage Ori. The vectors may also further include a single stranded replication origin.

The polynucleotide in the expression vector is operably linked to an appropriate expression control sequence(s) (promoter) to direct synthesis of the encoded gene product. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

In some embodiments, the promoter is inducible. Inducible promoters are well known in the art. Suitable inducible promoters include, but are not limited to, the pL of bacteriophage Plac; Ptrp; Ptac (Ptrp-lac hybrid promoter); an isopropyl-beta-D-thiogalactopyrahoside (IPTG) inducible promoter, e.g., a lacZ promoter; a tetracycline-inducible promoter; an arabinose inducible promoter, e.g., PBAD (see, e.g., Guzman et al. (1995) Bacteriol 177:4121-4130); a xylose-inducible promoter, e.g., PxyI (see, e.g., Kim et al. (1996) Gene 181: 71-76); a GAL™ promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda PL promoter, a promoter controlled by a heat-sensitive repressor (e.g., CI857-repressed lambda-based expression vectors; see, e.g., Hoffmann et al. (1999) FEMS Microbiol Lett. 177(2):327-34); and the like.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), apagC promoter (Pulkkinen and Miller, J: Bacteriol., 1991: 173 (1): 86-93; Alpuche-Aranda et al., PNAS, 1992; 89(21): 10079-83), a nirB promoter (Harborn et al. (1992) Mol. Micro. 6:2805-2813), and the like (see, e.g., Dunstan et al. (1999) Infect. Immun. 67:5133-5141; McKelvie et al. (2004) Vaccine 22:3243-3255; and Chatfeld et al. (1992) Biotechnol 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) Infect. Immun. 70:1087-1096); an rpsM promoter (see, e.g., Valdivia and Falkow (1996). Mol. Microbiol. 22:367-378); a tet promoter (see, e.g., Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); an SP6 promoter (see, e.g., Melton et al. (1984; Nucl. Acids Res. 12:7035-7056); and the like. Further useful promoters for bacterial host cells include the promoter obtained from the *Streptomyces coelicolor* agarase gene (dagA), *Bacillus subtilis* levansucrase gene (sacB), *Bacillus licheniformis* alpha amylase (amyL), *Bacillus stearothermophilus* maltogenic amylase gene (amyM), *Bacillus amyloliquefaciens* alpha amylase gene (amyQ), *Bacillus licheniformis* penicillinase gene (penP), *Bacillus subtilis* xylA and xylB genes and prokaryotic beta-lactamase gene. These promoters are all well known in the art.

For filamentous fungal host cells suitable promoters include promoters obtained from *Aspergillus oryzae* TAKA amylase, *Rhizomucor miehei* aspartic proteinase, *Aspergillus niger* or awamori glucoamylase (glaA), *Rhizomucor miehei* lipase and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. H5 A Practical Approach, Ed. DM Glover, 1986, IRL Press, Wash., D.C.).

In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as *E. coli*. Generally, recombinant expression vectors will include origins of replication and selectable markers permitting transformation of the host cell, e.g., the ampicillin resistance gene of *E. coli*, the *S. cerevisiae* TRP 1 gene, etc.; and a promoter derived from a highly expressed gene to direct transcription of the biosynthetic pathway gene product-encoding sequence. Such promoters can be derived from operons encoding glycolytic enzymes such as 3-phosphoglycerate kinase (PGK), x-factor, acid phosphatase, or heat shock proteins, among others.

Generally, DNA sequences encoding the structural coding sequence can be assembled from cDNA fragments and short oligonucleotide linkers, or from a series of synthetic oligonucleotides, to provide a synthetic nucleic acid that is capable of being expressed from a recombinant transcriptional unit contained in a cell or in a cell-free transcription and translation system. "Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms.

Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the transformed host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

In some embodiments, a genetically modified host cell is one that is genetically modified with a nucleic acid comprising a nucleotide sequence encoding a single gene, such as a GPS synthase. In other embodiments, a subject host cell is genetically modified with a nucleic acid comprising nucleotide sequences encoding two or more gene products, such as additionally a terpene synthase.

Where the host cell is genetically modified to express two or more gene products in a biosynthetic pathway, nucleotide sequences encoding the two or more gene products can be contained on separate expression vectors or on a single expression vector. Where nucleotide sequences encoding the two or more gene products are contained in a single expression vector, in some embodiments, the nucleotide sequences can be operably linked to a common control element (e.g., a promoter).

In some embodiments, the vector includes a gene operably linked to an inducible promoter. In other embodiments, the vector includes a gene operably linked to a constitutive promoter. In some embodiments, where two or more genes are expressed, one can be operably linked to an inducible promoter, and one can operably linked to a constitutive promoter.

The nucleic acids can be maintained extrachromosomally, e.g., are maintained episomally. For example, in some embodiments, the nucleic acids are plasmids or other expression vectors that do not become integrated into the genome of the genetically modified host cell. In other embodiments, the nucleic acid is integrated into the genome of the genetically modified host cell. Integration includes multiple tandem integrations, multiple non-tandem integrations, targeted integration, and random integration.

While one skilled in the art is aware that numerous plasmids and vectors may be used to introduce genes encoding enzymes of interest into a host cell, some preferred embodiments are disclosed in the Examples and Figures herein.

C. Host Cells

In one embodiment, the invention also provides a host cell that expresses a recombinant GPP synthase as described above. The host cell can be eukaryotic or prokaryotic. Suitable host cells include, but are not limited to, fungi, filamentous fungi, yeast, algae and bacteria.

In some embodiments, the host cell is a eukaryotic cell. Suitable eukaryotic host cells include, but are not limited to, fungal cells, algal cells, insect cells, and plant cells. Suitable fungal host cells include, but are not limited to, yeast cells and filamentous fungal cells.

In one embodiment, the host cell is a filamentous fungus. The filamentous fungi host cells of the present invention include all filamentous forms of the subdivision *Eumycotina* and *Oomycota* (Hawksworth et al., 1995, in *Ainsworth and Bisby's Dictionary of The Fungi*, 8th ed.). Filamentous fungi are characterized by a vegetative mycelium with a cell wall composed of chitin, cellulose, and other complex polysaccharides. As used herein, the filamentous fungi host cells of the present invention are morphologically distinct from yeast. Exemplary filamentous fungal cells include, but are not limited to, species of: *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, synonyms or taxonomic equivalents thereof.

In some embodiments, the filamentous fungal host cell is a species of: *Aspergillus* (e.g., *A. awamori, A. fumigatus, A. japonicus, A. nidulans, A. niger, A. aculeatus, A. foetidus, A. oryzae* and *A. kawachi*); *Chrysosporium* (*C. lucknowense, C. keratinophilum, C. tropicum, C. merdarium, C. inops, C. pannicola*, and *C. zonatum*); *Fusarium* (e.g., *F. bactridioides, F. cerealis, F. crookwellense, F. culmorum, F. graminearum, F. graminum, F. oxysporum, F. roseum*, and *F. venenatum*); *Myceliophthora* (e.g., *M. thermophilia*); *Neurospora* (e.g., *N. crassa*); or *Trichoderma* (*T. longibrachiatum, T. viride, Hypocrea jecorina* or *T. reesei*).

In one embodiment, the microbial organism is a yeast. In one embodiment, the yeast is from one of the genera: *Candida, Hansenula, Saccharomyces, Schizosaccharomyces, Pichia, Kluyveromyces*, and *Yarrowia*. In some embodiments, the yeast cell is *Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

In some embodiments, the host cell is an algal cell such as *Chlamydomonas* (e.g., *C. Reinhardtii*) and *Phormidium* (P. sp. ATCC29409).

In other embodiments, the host cell is a prokaryotic cell. Suitable prokaryotic cells include gram positive, gram negative and gram-variable bacterial cells. Exemplary prokaryotic host cells include, but are not limited to, species of: *Agrobacterium, Alicyclobacillus, Anabaena, Anacystis, Acinetobacter Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmun, Streptomyces, Streptococcus, Synnecoccus, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* and *Zymomonas*.

In some embodiments, the bacterial host cell is non-pathogenic to humans. In some embodiments, the bacterial host strain is an industrial strain. Numerous bacterial industrial strains are known and suitable in the present invention.

In some embodiments, the bacterial host cell is of the *Bacillus* species, e.g., *B. thuringiensis, B. megaterium, B. subtilis, B. lentus, B. circulans, B. pumilus, B. lautus, B. coagulans, B. brevis, B. licheniformis, B. clausii, B. stearothermophilus* and *B. amyloliquefaciens*. In some embodiments, the bacterial host cell is of the *Clostridium* species, e.g., *C. acetobutylicum, C. tetani* E88, *C. lituseburense, C. saccharobutylicum, C. perfringens*, and *C. beijerinckii*. In some embodiments, the bacterial host cell is of the *Corynebacterium* species e.g., *C. glutamicum* and *C. acetoacidophilum*. In some embodiments, the bacterial host cell is of the *Escherichia* species, e.g., *E. coli*. In some embodiments the bacterial host cell is of the *Erwinia* species, e.g., *E. uredovora, E. carotovora, E. ananas, E. herbicola, E. punctata*, and *E. terreus*. In some embodiments, the bacterial host cell is of the *Pantoea* species, e.g., *P. citrea* and *P. agglomerans*. In some embodiments, the bacterial host cell is of the *Pseudomonas* species, e.g., *P. pudita, P. mevalonii*, and *P*. sp. D-0110. In some embodiments, the bacterial host cell is of the *Streptococcus* species, e.g., *S. equisimiles, S. pyogenes*, and *S. uberis*. In some embodiments, the bacterial host cell is of the *Streptomyces* species, e.g., *S. ambofaciens, S. avermitilis, S. coelicolor, S. aureofaciens, S. aureus, S. fungicidicus, S. griseus*, and *S. lividans*. In some embodiments, the bacterial host cell is of the *Zymomonas* species, e.g., *Z. mobilis* and *Z. lipolytica*.

Strains that may serve as suitable host cells, including both prokaryotic and eukaryotic strains, are readily accessible to the public from a number of culture collections such as American Type Culture Collection (ATCC), Deutsche Sammlung von Mikroorganismen and Zellkulturen GmbH (DSM), centraalbureau Voor Schimmelcultures (CBS), and Agricultural Research Service Patent Culture Collection, Northern Regional Research Center (NRRL).

D. Additional Metabolic Engineering

The host cell can be further modified to produce one or more desired monoterpenes. For example, the host cell can be selected or engineered to co-express one or more terpene synthases. The terpene synthase can be an endogenous enzyme or a heterologous enzyme. For example, one can select a host cell that naturally produces a terpene synthase. Alternatively, a host cell can be transformed with a polynucleotide encoding a terpene synthase. The terpene synthase can be one that forms a non-cyclic monoterpene product or a cyclic monoterpene product. In some embodiments, the terpene synthase is a cyclic terpene synthase capable of producing a combination of monocyclic, bicyclic, and tricyclic products. Exemplary terpene synthases include, but are not limited to, bornyl diphosphate synthases, camphene synthases, and sabinene synthase.

In one embodiment, the terpene synthase is a variant terpene synthase as disclosed in U.S. Application 61/319,560. In one embodiment, the terpene synthase comprises a polypeptide sequence that has at least 80% sequence identify with a wild-type terpene synthase. The wild-type terpene synthase can be a bornyl diphosphate synthase (BPS), e.g., a BPS from *Salvia officinalis* (BPS-SOFF, NCBI Accession No. AAC26017) or *Rosemarinus officinalis* (BPS-ROFF, NCBI Accession No. ABP01684.1); a camphene synthase (CamS), e.g., a CamS from *Pseudotsuga menzeseii* (CamS-PMEN, NCBI Accession No. AAX07267.1) or Abies grandis (CamS-AGR, NCBI Accession No. AAB70707.1); a TPS10 enzyme such as from *Arabidopsis thaliana* (NCBI Accession No. NP_179998.1); a limonene synthase such as from *Mentha spicata* (LS-MSPI, NCBI Accession No. AAC37366.1); a pinene synthase such as those from *Artemisia annua* (PS-AANN, NCBI Accession No. AAK58723.1); a fenchol synthase such as those from *Ocimym basilicum* (FS-OBAS, NCBI Accession No. AAV63790.1); or a 1,8 cineole synthase such as those from *Salvia fruticosa* (CS-SFRU, NCBI Accession No. ABH07677.1). In one embodiment, the terpene synthase has an amino acid substitution corresponding to one or more of positions 270, 294, 366, 373, 404, 414, 460, and 525 of wild-type BPS-SOFF.

In some embodiments, the entire mevalonate pathway needs to be expressed in the host cell (e.g., *E. coli*) to produce terpenes because the cell does not express the entire mevalonate pathway. Alternatively, if the cells (e.g., *E. coli*) are provided with mevalonate, only genes for the lower mevalonate pathway need to be expressed in order to produce terpenes. Thus, depending on the organism used, one can supply the needed genes required for the production of terpenes. In the Examples below, the nucleotide sequences of the wild-type GPP synthase and the recombinant GPP synthases were expressed along with the lower mevalonate pathway to produce terpenes for the reporter assay.

V. Cell Culture

"Culturing" or "cultivation" refers to growing a population of microbial cells under suitable conditions in a liquid or solid medium. In particular embodiments, culturing refers to the fermentative bioconversion of a substrate to an end-product. Conditions for the culture and production of cells, including filamentous fungi, bacterial, and yeast cells, are readily available. Cell culture media in general are set forth in Atlas and Parks, eds., 1993, *The Handbook of Microbiological Media*. The individual components of such media are available from commercial sources.

In one embodiment, the culture medium contains fermentable sugars. Fermentable sugars are sugars that may be metabolized by a host cell. Fermentable sugars may be five-carbon (C5) sugars, six-carbon (C6) sugars, and/or oligomers of C6 and C5 sugars. Examples include, but are not limited to, glucose, fructose, sucrose, maltose, xylose, arabinose, galactose, mannose, raffinose and combinations thereof. Fermentable sugars are derived from the hydrolysis of carbohydrate polymers such as cellulose and starch. Sources of starch include plant material (such as leaves, stems, leaves, roots and grain, particularly grains derived from but not limited to corn, wheat, barley, rice, and sorghum. Exemplary feedstocks may be obtained from alfalfa, corn stover, crop residues, debarking waste, forage grasses, forest residues, municipal solid waste, paper mill residue, pomace, scraps & spoilage (fruit & vegetable processing), sawdust, spent grains, spent hops, switchgrass, waste wood chips, wood chips.

The molecular form which the digestible carbon is available in varies with the choice of feedstock. Some feedstocks will have the majority of carbon available in cellulose. Other feedstocks will have a significant amount of carbon available in hemicellulose. Many feedstocks will contain lignin as well as cellulose. In some instances the lignocellulose feedstock can be pretreated using heat, acid treatment or base treatment. Therefore, the choice of feedstock degrading peptides used can be optimized depending on the structure of the chosen feedstock and whether a pretreatment is used. Possible pretreatments include the use of dilute acid, steam explosion, ammonia fiber explosion (AMFE), organic solvents (Bio-Cycle, May 2005 News Bulletin, and see: Ethanol from Cellulose: A General Review, P. Badger, p. 17-21 in J. Janick and A. Whipkey (eds.), Trends in New Crops and Uses, ASHS Press, 2002).

A. Improved GPP and Monoterpene Production

In one embodiment of the invention, the recombinant GPP synthase exhibits improved GPP production compared to a reference prenyl transferase. The reference prenyl transferase can be, e.g. *E. coli* IspA enzyme (SEQ ID NO: 2) or a variant *E. coli* IspA enzyme (SEQ ID NO: 3). In one embodiment, the GPP production is improved more than 1-, 2-, 3-, 4-, or 5-fold over the reference prenyl transferase. In one embodiment, GPP production is improved 0.1- to 5-fold, 0.1- to 3-fold, 1- to 5-fold, or 1- to 3-fold over the reference prenyl transferase.

In one embodiment, the reference prenyl transferase is SEQ ID NO: 3. This IspA S80F variant (S81F in Reiling et al., *Biotechnology and Bioengineering* 87(2):200-212 (2004)) is a suitable positive control for comparing IspA activity (GPP synthase activity). IspA S80F produces readily measurable amounts of monoterpenoid (e.g. sabinene) in a GC-FID assay.

The wild-type IspA accumulates so little GPP compared to FPP (its FPP synthase activity tends to supersede its GPP synthase activity) that GPP synthase activity is difficult to measure using the sabinene assay, making it a less suitable reference for comparing GPP synthase activity in modified IspA enzymes.

In another embodiment, the recombinant GPP synthase exhibits improved GPP selectivity compared to the reference prenyl transferase. In one embodiment, the recombinant GPP synthase produces more GPP than FPP. In some embodiments, the recombinant GPP synthase, when expressed in a host cell as described herein, produces a GPP: FPP ratio of at least 1:1, at least 2:1, at least 3:1, or at least 4:1.

In one embodiment, improved GPP production can be assessed by co-expressing a terpene synthase capable of converting GPP to a terpene (e.g., a monoterpene). Thus, GPP production is measured indirectly by measuring the resulting monoterpene product. Similarly, a host cell may also express a terpene synthase capable of converting GPP to a terpene having greater than 15 carbons. Thus, other terpene precursors (such as FPP) can also be measured indirectly by measuring the resulting terpenes (C15+) products. A carotenoid reporter system, for example, detects larger terpenes. Thus, GPP production as well as GPP production relative to FPP production can be measured. The terpene products may be produced as a reporter system and/or the they may be produced and recovered for use in compositions such as fuel compositions. Accordingly, a method of producing GPP and/or terpenes according to the present invention may also include detecting, measuring, and/or recovering terpenes (e.g., monoterpenes). And the methods may include improved monoterpene production in addition to improved GPP production.

The variant libraries described herein were screened with the monoterpene reporter sabinene synthase. This cyclic terpene synthase was selected because the major monoterpene product (sabinene) can be rapidly quantified by gas chromatography-flame ionization detector (GC-FID) analysis. In this reporter system, increased production of sabinene indicates increased production of GPP. Other monoterpenes could be used in place of sabinene as reporter compounds, as will be apparent to the person of ordinary skill in the art. Specifically, although this monoterpene reporter and screen was developed in *E. coli*, these methods could be readily adapted to other expression systems (e.g., yeast, fungi, etc.).

B. Recovery

In one embodiment, the method includes a step of recovering the GPP produced by the recombinant GPP synthase. The GPP produced by a host cell can be recovered for use in other reactions or other host cells.

In another embodiment, the method includes a step of recovering one or more terpene products. Suitable protocols for recovering monoterpenes from recombinant host cells and/or culture medium are known to the skilled artisan. For example, wherein the aqueous medium comprises a first phase, recovering can include forming a liquid organic second phase or adding a liquid organic second phase in which the monoterpene is concentrated. The method further includes separating at least a portion of the second phase from the first phase and isolating the monoterpene from the second phase. Organic compositions that can be added to the first phase include, but are not limited to hexane, heptanes, decane, dodecane, hexadecane, ethyl acetate and methyl-t-butyl ether. In addition, hydrophobic resins such as Tenax or XAD resins can be useful to isolate the monoterpene. WO 2007/139924 expressly incorporated by reference herein describes a system for separating terpenes from aqueous media.

The method may include one or more additional processing components including one or more separation systems for separating the monoterpene from the aqueous media and the organic second phase, one or more reactors for biologically or chemically altering the monoterpene such as by addition, substitution, hydrogenation, alkylation, hydroxylation, condensation, halogenation or any other suitable reaction, one or more blending vessels or systems for blending the monoterpene with one or more additional components, and one or more additional purification or separation systems for further purifying the monoterpene.

The monoterpene may be isolated from the first phase and/or second phase using any suitable separation method. In some embodiments, the organic second phase occurs spontaneously as a result of chemical and molecular interactions such as differences in solubility, or hydrophobicity, density, concentration or any other spontaneous phase separation mechanism. In other embodiments, separation of the first and second phases is induced in a separation vessel or vessels or system that may be the same or a different vessel or vessels or processing system as the fermentation vessel or vessels. In some embodiments, phase separation is induced by centrifugation and/or by the introduction of a demulsifier or a nucleating agent into the fermentation reaction.

Once phase separation occurs, the separate phases can be individually drawn from the separation vessel.

In some embodiments, the monoterpene may be isolated from the organic second phase using adsorption, a process in which molecules move from a bulk liquid onto the surface of adsorbents. Isolation by adsorption may be performed using a batch, continuous or semi-continuous process. In other embodiments, the monoterpene may be isolated from the organic second phase using distillation, a method of separating substances based on differences in their volatilities. In other embodiments, the monoterpene is isolated from the organic second phase using gas-liquid extraction. This process is also known as stripping and is the transfer of a component dissolved in a liquid stream into a vapor stream in a more concentrated form. In other embodiments, the monoterpene is isolated from the organic second phase using liquid-liquid extraction. Also known as solvent extraction, liquid-liquid extraction is the transfer of a substance from one liquid phase into another immiscible liquid phase.

In a batch liquid-liquid extraction system, the feed liquid (the organic second phase) is mixed with a second immiscible liquid phase in a suitable vessel. The mixture is then permitted to settle into layers and separate into extract and raffinate and the lighter layer can be decanted from the vessel. The desired monoterpene can be in the extract or raffinate depending on the product and solvent used.

In a continuous liquid-liquid extraction system, differences in density, vapor pressure at a given temperature, or boiling points are used to separate the desired monoterpene from the feed liquid (the organic phase). Such systems can use mixer/settler tanks, towers or columns, centrifuges and combinations thereof to effect separation.

In other embodiments, the monoterpene is isolated from the organic second and/or the aqueous first phase using ultrafiltration, a pressure-driven membrane process used to separate solution components on the basis of molecular size and shape.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

TABLE 1

Genes in the pCEN0067 plasmid

| Gene | Description |
|---|---|
| PLtetO-1 | Lambda phage promoter with tet operator sites acting as repressive elements |
| mvaK1 | Mevalonate kinase [mvk] [*Streptococcus pneumoniae* (strain ATCC BAA-255/R6)] AAK99142.1 |
| mvaK2 | Phosphomevalonate kinase [mvaK2] [*Streptococcus pneumoniae* (strain ATCC BAA-255/R6)] AAK99144.1 |
| mvaD | Diphosphomevalonate decarboxylase [mvd1] (EC 4.1.1.33) [*Streptococcus pneumoniae* (strain ATCC BAA-255/R6)] AAK99143.1 |
| Idi | Isopentenyl-diphosphate Delta-isomerase [idi] (EC 5.3.3.2) (IPPisomerase) (Isopentenyl pyrophosphate isomerase)(IPP:DMAPP isomerase) [*Escherichia coli* (strain K12)] AAC75927.1 |
| ispAs80F | Geranyltransferase [ispAS80F] (EC 2.5.1.10) (Farnesyl-diphosphate synthase) (FPP synthase) S80F mutation [*Escherichia coli* (strain K12)] Reiling KK et al., Biotechnology and Bioengineering 87(2): 200-212 (2004) SEQ ID NO: 3 |
| KanR | Aminoglycoside 3'-phosphotransferase [neo] (EC 2.7.1.95) (Kanamycin kinase, type II) (Neomycin-kanamycin phosphotransferase type II) (APH(3')-II) (APH(3')II) [*Klebsiella pneumoniae*] |

TABLE 2

Genes in the pCK110900-I-SOFF plasmid

| Gene | Description |
|---|---|
| P15A | P15A origin derived from pACYC |
| SS SOFF | (+)-sabinene synthase, chloroplastic precursor (EC 4.2.3.11) (SSS) [*Salvia officinalis* (Sage)] AAC26018.1. |

Example 1

Plasmid Construction

Plasmid pCEN0067 (FIG. 3) was constructed to encode enzymes of the lower mevalonate pathway and the prenyl transferase (GPP). This high copy plasmid contains the genes mvaK1 (AAK99142.1), mvaK2 (AAK99144.1), and mvaD (AAK99143.1) from *S. pneumoniae*, and idi (AAC75927.1) and ispA-S80F (SEQ ID NO: 3) from *E. coli* under control of the tetracycline inducible promoter PLtetO-1 in the vector pZE21 MCS (Expressys, Ruelzheim, Germany). Restriction sites suitable for the introduction of the lower mevalonate pathway genes were first engineered into pZE21MCS. The original multiple cloning site (MCS) fragment was replaced with a new MCS fragment containing restriction sites for cloning each of the pathway genes. The new MCS was generated by annealing the following oligonucleotides;

MevMCS-F-
(SEQ ID NO: 4)
5'-gaattcataagcttgtgagcggccgcattgatgcatagctagcaggc cggccaggtaccac-3'
and MevMCS-R-
(SEQ ID NO: 5)
5'-cccgggtggtacctggccggcctgctagctatgcatcaatgcggccg ctcacaagcttatg-3'.

This fragment was ligated into pZE21MCS digested with EcoRI and XmaI to create pCEN0054 which was used to clone the lower mevalonate pathway.

The mvaK1, mvaK2, and mvaD genes from *S. pneumoniae* were designed with a codon bias optimized for expression in *E. coli*, synthesized (Gene Oracle), and cloned into pCEN0054 using conventional cloning procedures to generate pCEN0067.

Plasmid pCEN0202, which expresses the wild-type ispA gene, was created from pCEN0067. Site-directed mutagenesis was used to convert the IspA-S80F nucleotide sequence back to the wild-type sequence. pCEN0202 served as the template for constructing the ispA libraries in the subsequent examples.

Figure 3:
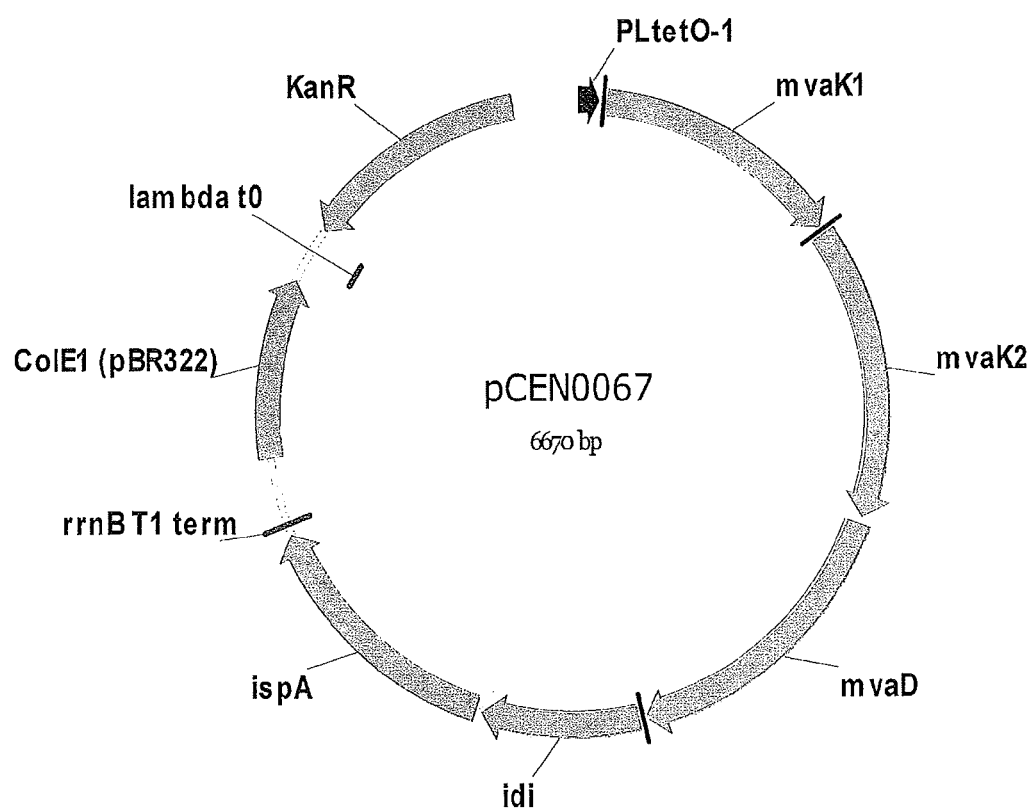
FIG. 3 shows plasmid pCEN0067 comprising PLtetO-1 Lambda phage promoter with tet operator sites, mevalonate kinase (mvaK1), mevalonate kinase2 (mvaK2), Diphosphomevalonate decarboxylase (mvaD), Isopentenyl-diphosphate Delta-isomerase (idi), GPP synthase (IspAS80F) (SEQ ID NO: 3), and kanamycin resistance gene (KanR).
Figure 4:
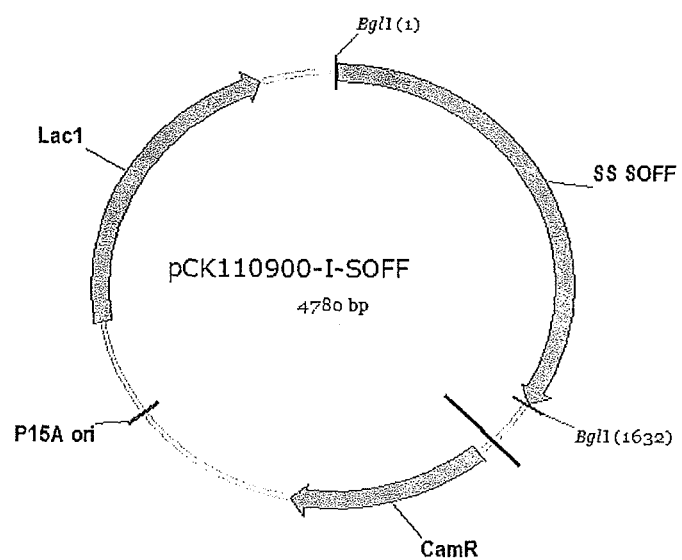
FIG. 4 shows plasmid pCK110900-1-SOFF comprising sabinene synthase from Salvia officinalis (Sage) to be used in the monoterpene production assays.

The sabinene synthase gene from *Salvia officinalis* (SS-SOFF) was cloned into the expression vector pCK110900-I (See FIG. 3 of PCT publication WO 05/017135 and corresponding U.S. Pat. No. 7,629,157). The gene coding for the SS-SOFF synthase (AAC26018.1) was codon altered for expression in *E. coli* and synthesized with flanking BgII restriction sties used for cloning into the pCK110900-I vector to generate plasmid pCK1109900-1-SOFF (FIG. 4).

Example 2

Expression and Monoterpene Assay Methods

Growth and Harvest

To obtain strains for monoterpene production, *E. coli* W3110Z1 cells from Expressys were first transformed with plasmid pCK110900-I-SOFF (FIG. 4). These cells were then made electro competent using established molecular biology protocols and transformed with a pCEN0202 based library of ispA variants. The transformants were plated on LB agar plates containing 30 µg/ml chloramphenicol (CAM) and 40 µg/ml kanamycin (Kan).

Cells were picked from transformed colonies and grown in 96-well shallow flat bottom plates with 180 µl/well of Lysogeny Broth (LB) media containing 1% glucose, 30 µg/ml chloroamphenicol (CAM) and 40 µg/ml kanamycin (Kan). Plates were grown overnight at 30° C., and 85% relative humidity and shaken at 200 rpm. 20 µL of overnight growth was used to inoculate a 96-deep-well plate with 380 µL/well of terrific broth (TB) containing 30 µg/ml CAM and Kan 40 µg/ml. The plates were covered with airpore tape, and shaken at 200 rpm, 30° C., and 85% humidity for 2 hours. Mevalonate, isopropyl β-D-1-thiogalactopyranoside (IPTG), and anhydro-tetracycline were added to a final concentration of 20 mM, 1 mM, and 100 ng/ml, respectively. 40 µl of dodecane was added to each well. The plates were heat sealed at 178° C. for 2.5 sec and shaken at 200 rpm, 30° C., and 85% humidity for 2 days (~40 hrs). 360 µl of ethyl acetate with 0.15 mg/ml of 3-nitrobenzaldehyde (NBA) was added to each well. The plates were sealed, shaken for 30 minutes, and spun down for 10 min at 4° C. and 4000 rpm. 80 μl of the top ethyl acetate layer was extracted from each well and analyzed by GC-FID.

GC-FID Sabinene Detection Method

Samples were analyzed on an Agilent Technologies 6890N Network GC systems GC-FID. The GC was fitted with an HP-5 30 m, 0.25 um film, 320 uM ID column and operated under the following conditions: inlet temperature, 300° C.; split ratio, 2:1; detector temperature, 300° C., H₂ flow, 40 ml/min; air flow, 400 ml/min; N₂ makeup flow 40 ml/min. The FID oven was set to an initial temperature of 90° C. and ramped to 100° C. at a rate of 35° C./min. The temperature was further ramped up to 250° C. at a rate of 80° C./min and kept at 250° C. until the end of the run.

Example 3

Recombinant IspA Variants

The gene for wild-type *E. coli* IspA was obtained from *Escherichia coli* (strain K12) NP_414955.1 (SEQ ID NO: 1) and the protein sequence (SEQ ID NO: 2) was used as a template for constructing DNA libraries. Libraries of ispA variants were ligated into the BgII cloning sites in the pCEN0202 vector, replacing the wild-type IspA gene. Screening of the libraries was carried out using the procedure outlined in example 2.

A variant of IspA having the amino acid change S80F was used as a positive control. This variant has previously been shown to provide improved GPP synthase activity over the corresponding wild-type IspA. See Reiling et al., 2004. This variant is readily detectable as a GPP synthase in the sabinene synthase assay described herein, and accordingly is a suitable reference enzyme for evaluating the GPP synthase activity of other IspA variants.

For the wild-type ispA enzyme, the reaction proceeds so quickly and predominantly to FPP that the level of sabinene produced from GPP was not detectable (N.D.). Other than the wild-type enzyme, the amino acid changes for the variants listed in Table 3 produced a quantifiable amount of sabinene. Activity is shown relative to the ispA-S80F (Variant No. 1) previously shown to produce GPP in addition to FPP. See, e.g. Reiling et al., (2004). The reference activity of IspAS80F was set at a value of 1. Data from all the replicates was averaged. A relative activity of more than 1 indicates a variant that is more selective for GPP than IspAS80F (Variant No. 1). A relative activity of less than 1 indicates a variant that is less selective for GPP than IspAS80F (Variant No. 1), but is still improved over wild-type IspA.

TABLE 3

Variants of *E. coli* IspA with Improved GPP Synthase Activity

| Variant Number | Amino Acid Changes | Relative Activity to IspA-S80F (Variant 1) |
|---|---|---|
| 1 | S80F | 1.0 |
| 2 | L112Y, R136C, I139V, Q158M, A159M | 2.00 |
| 3 | L112F, Q158M, L162M | 1.21 |
| 4 | M154H, A159T | 1.06 |
| 5 | L112H, Q158M | 2.49 |
| 6 | L112F, A159M, L162M, L290P | 1.00 |
| 7 | M154W | 0.94 |
| 8 | L112W | 0.88 |
| 9 | V32A, L112F, Q158M, A159M | 0.87 |
| 10 | Q158F | 0.78 |
| 11 | H102R, M154F, A241V | 0.77 |
| 12 | P99S, M154W, A241V | 0.77 |
| 13 | L112Y, Q158M | 0.72 |
| 14 | M154Y | 0.70 |
| 15 | L112R | 0.70 |
| 16 | Q158L, A241V | 0.64 |
| 17 | L112F, Q158M | 0.63 |
| 18 | Q158L | 0.61 |
| 19 | L112R, A241V | 0.59 |
| 20 | L112F, K237N | 0.57 |
| 21 | I76V, L112F, A159S | 0.56 |
| 22 | L112H, Q158R, A159M, A241V | 0.55 |
| 23 | A54V, L112H, G201E | 0.51 |
| 24 | L112F, A159S, L162M, K237R | 0.51 |
| 25 | L112H, L162M, S285P | 0.51 |
| 26 | M154H, A241V | 0.50 |
| 27 | Q158W | 0.50 |
| 28 | L112F, Q118P | 0.50 |
| 29 | Q28R, L112R | 0.48 |
| 30 | L112F | 0.47 |
| 31 | L112F, L162M | 0.45 |
| 32 | Wild-type | N.D. |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A recombinant geranyl diphosphate (GPP) synthase comprising a polypeptide sequence having at least 90% sequence identity to SEQ ID NO: 2, and having an amino acid substitution at one or both of positions M 154 and Q 158 of SEQ. ID NO: 2.

2. The GPP synthase of claim 1, further comprising the amino acid substitution S 80F.

3. The GPP synthase of claim 1, wherein the amino acid at position M 154 is histidine, tyrosine, phenylalanine, tryptophan, or arginine.

4. The GPP synthase of claim 3, wherein the amino acid at position M 154 is histidine, tyrosine, or tryptophan.

5. The GPP synthase of claim 1, wherein the amino acid at position Q 158 is methionine, phenylalanine, leucine, or tryptophan.

6. The GPP synthase of claim 1, further comprising an amino acid substitution at position L 112.

7. The GPP synthase of claim 6, wherein the amino acid at position 112 is histidine, tyrosine, phenylalanine, tryptophan, or arginine.

8. The GPP synthase of claim 7, wherein the amino acid at position 112 is histidine or tyrosine.

9. The GPP synthase of claim 1, further comprising an amino acid substitution at one or more of positions V 32, A 54, 176, P 99, R 136, 1139, A 159, L 162, G 201, K 237, A 241, and L 290.

10. The GPP synthase of claim 9, comprising at least one amino acid substitution from among V 32A, A 54V, I 76V, P 99S, R 136C, 1139V, A 159M, A 159S, L 162M, G 201 Q, K 237N, A 241V, and L 290P.

11. The GPP synthase of claim 9, comprising an amino acid substitution corresponding to position A 159 and/or L 162.

12. The GPP synthase of claim 1 comprising a variant disclosed in Table 3.

13. The GPP synthase of claim 1, having at least 95% sequence identity to SEQ ID NO: 2.

14. The GPP synthase of claim 13, having at least 99% sequence identity to SEQ ID NO: 2.

15. The GPP synthase of claim 1, wherein the GPP synthase exhibits improved GPP production compared to SEQ ID NO: 2 or SEQ ID NO: 3 when expressed in *E. coli* under the same culture conditions.

16. The GPP synthase of claim 15, wherein the GPP synthase exhibits improved GPP selectivity compared to SEQ ID NO: 2 or SEQ ID NO: 3 when expressed in *E. coli* under the same culture conditions.

17. A polynucleotide encoding a recombinant GPP synthase of claim 1.

18. A vector incorporating the polynucleotide of claim 17.

19. A host cell comprising the polynucleotide of claim 17.

20. The host cell of claim 19, wherein the host cell is *E. coli*.

21. A method of producing geranyl diphosphate in a host cell comprising a) expressing the polynucleotide of claim 17 in a host cell capable of converting isopentenyl pyrophosphate (IPP) and dimethyl pyrophosphate (DMAPP) to geranyl diphosphate (GPP), and b) culturing the host cell under conditions in which the geranyl diphosphate synthase acts on IPP and/or DMAPP to produce GPP.

22. The method according to claim 21, wherein the host cell is *E. coli*.

23. The method according to claim 21, further comprising introducing a vector according to claim 19 into the host cell.

24. The method of claim 21, further comprising reacting the geranyl diphospahte with a monoterpene synthase to produce monoterpenes.

25. The method of claim 24, wherein the monoterpene synthase is a cyclic monoterpene synthase.

26. The method of claim 24 further comprising recovering the monoterpenes.

* * * * *

SEQUENCE LISTING

```
<160> NUMBER OF SEQ ID NOS: 14

<210> SEQ ID NO 1
<211> LENGTH: 900
<212> TYPE: DNA
<213> ORGANISM: Escherichia coli

<400> SEQUENCE: 1
atggactttc cgcagcaact cgaagcctgc gttaagcagg ccaaccaggc gctgagccgt      60
tttatcgccc cactgcccct tcagaacact cccgtggtcg aaaccatgca gtatggcgca     120
ttattaggtg gtaagcgcct gcgacctttc ctggtttatg ccaccggtca tatgttcggc     180
gttagcacaa acacgctgga cgcacccgct gccgccgttg agtgtatcca cgcttactca     240
```

-continued

```
ttaattcatg atgatttacc ggcaatggat gatgacgatc tgcgtcgcgg tttgccaacc    300
tgccatgtga agtttggcga agcaaacgcg attctcgctg gcgacgcttt acaaacgctg    360
gcgttctcga ttttaagcga tgccgatatg ccggaagtgt cggaccgcga cagaatttcg    420
atgatttctg aactggcgag cgccagtggt attgccggaa tgtgcggtgg tcaggcatta    480
gatttagacg cggaaggcaa acacgtacct ctggacgcgc ttgagcgtat tcatcgtcat    540
aaaaccggcg cattgattcg cgccgccgtt cgccttggtg cattaagcgc cggagataaa    600
ggacgtcgtg ctctgccggt actcgacaag tatgcagaga gcatcggcct tgccttccag    660
gttcaggatg acatcctgga tgtggtggga gatactgcaa cgttgggaaa acgccagggt    720
gccgaccagc aacttggtaa aagtacctac cctgcacttc tgggtcttga gcaagcccgg    780
aagaaagccc gggatctgat cgacgatgcc cgtcagtcgc tgaaacaact ggctgaacag    840
tcactcgata cctcggcact ggaagcgcta gcggactaca tcatccagcg taataaataa    900
```

<210> SEQ ID NO 2
<211> LENGTH: 299
<212> TYPE: PRT
<213> ORGANISM: Escherichia coli

<400> SEQUENCE: 2

```
Met Asp Phe Pro Gln Gln Leu Glu Ala Cys Val Lys Gln Ala Asn Gln
 1               5                  10                  15

Ala Leu Ser Arg Phe Ile Ala Pro Leu Pro Phe Gln Asn Thr Pro Val
             20                  25                  30

Val Glu Thr Met Gln Tyr Gly Ala Leu Leu Gly Gly Lys Arg Leu Arg
         35                  40                  45

Pro Phe Leu Val Tyr Ala Thr Gly His Met Phe Gly Val Ser Thr Asn
     50                  55                  60

Thr Leu Asp Ala Pro Ala Ala Val Glu Cys Ile His Ala Tyr Ser
 65                  70                  75                  80

Leu Ile His Asp Asp Leu Pro Ala Met Asp Asp Asp Leu Arg Arg
                 85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Lys Lys Ala Arg Asp Leu Ile Asp Asp Ala Arg Gln
```

```
                    260                 265                 270
Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
    290                 295

<210> SEQ ID NO 3
<211> LENGTH: 299
<212> TYPE: PRT
<213> ORGANISM: Artificial sequence
<220> FEATURE:
<223> OTHER INFORMATION: Synthetic polypeptide of S80F variant of WT
      IspA from Escherichia coli

<400> SEQUENCE: 3

Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Val Glu Cys Ile His Ala Tyr Phe
65                  70                  75                  80

Leu Ile His Asp Asp Leu Pro Ala Met Asp Asp Asp Asp Leu Arg Arg
                85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Lys Lys Ala Arg Asp Leu Ile Asp Asp Ala Arg Gln
            260                 265                 270

Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
    290                 295

<210> SEQ ID NO 4
<211> LENGTH: 61
<212> TYPE: DNA
```

-continued

<213> ORGANISM: Artificial sequence
<220> FEATURE:
<223> OTHER INFORMATION: Synthetic oligonucleotide

<400> SEQUENCE: 4
gaattcataa gcttgtgagc ggccgcattg atgcatagct agcaggccgg ccaggtacca    60
c    61

<210> SEQ ID NO 5
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 5
cccgggtggt acctggccgg cctgctagct atgcatcaat gcggccgctc acaagcttat    60
g    61

<210> SEQ ID NO 6
<211> LENGTH: 367
<212> TYPE: PRT
<213> ORGANISM: Gallus gallus

<400> SEQUENCE: 6

```
Met His Lys Phe Thr Gly Val Asn Ala Lys Phe Gln Gln Pro Ala Leu
1               5                   10                  15

Arg Asn Leu Ser Pro Val Val Glu Arg Glu Arg Glu Phe Val
            20                  25                  30

Gly Phe Phe Pro Gln Ile Val Arg Asp Leu Thr Glu Asp Gly Ile Gly
        35                  40                  45

His Pro Glu Val Gly Asp Ala Val Ala Arg Leu Lys Glu Val Leu Gln
    50                  55                  60

Tyr Asn Ala Pro Gly Gly Lys Cys Asn Arg Gly Leu Thr Val Val Ala
65                  70                  75                  80

Ala Tyr Arg Glu Leu Ser Gly Pro Gly Gln Lys Asp Ala Glu Ser Leu
                85                  90                  95

Arg Cys Ala Leu Ala Val Gly Trp Cys Ile Glu Leu Phe Gln Ala Phe
            100                 105                 110

Phe Leu Val Ala Asp Asp Ile Met Asp Gln Ser Leu Thr Arg Arg Gly
        115                 120                 125

Gln Leu Cys Trp Tyr Lys Lys Glu Gly Val Gly Leu Asp Ala Ile Asn
    130                 135                 140

Asp Ser Phe Leu Leu Glu Ser Ser Val Tyr Arg Val Leu Lys Lys Tyr
145                 150                 155                 160

Cys Arg Gln Arg Pro Tyr Tyr Val His Leu Leu Glu Leu Phe Leu Gln
                165                 170                 175

Thr Ala Tyr Gln Thr Glu Leu Gly Gln Met Leu Asp Leu Ile Thr Ala
            180                 185                 190

Pro Val Ser Lys Val Asp Leu Ser His Phe Ser Glu Glu Arg Tyr Lys
        195                 200                 205

Ala Ile Val Lys Tyr Lys Thr Ala Phe Tyr Ser Phe Tyr Leu Pro Val
    210                 215                 220

Ala Ala Ala Met Tyr Met Val Gly Ile Asp Ser Lys Glu Glu His Glu
225                 230                 235                 240

Asn Ala Lys Ala Ile Leu Leu Glu Met Gly Glu Tyr Phe Gln Ile Gln
                245                 250                 255
```

-continued

Asp Asp Tyr Leu Asp Cys Phe Gly Asp Pro Ala Leu Thr Gly Lys Val
            260                 265                 270

Gly Thr Asp Ile Gln Asp Asn Lys Cys Ser Trp Leu Val Val Gln Cys
        275                 280                 285

Leu Gln Arg Val Thr Pro Glu Gln Arg Gln Leu Leu Glu Asp Asn Tyr
    290                 295                 300

Gly Arg Lys Glu Pro Glu Lys Val Ala Lys Val Lys Glu Leu Tyr Glu
305                 310                 315                 320

Ala Val Gly Met Arg Ala Ala Phe Gln Gln Tyr Glu Glu Ser Ser Tyr
                325                 330                 335

Arg Arg Leu Gln Glu Leu Ile Glu Lys His Ser Asn Arg Leu Pro Lys
            340                 345                 350

Glu Ile Phe Leu Gly Leu Ala Gln Lys Ile Tyr Lys Arg Gln Lys
        355                 360                 365

<210> SEQ ID NO 7
<211> LENGTH: 299
<212> TYPE: PRT
<213> ORGANISM: Salmonela enterica

<400> SEQUENCE: 7

Met Asp Phe Thr Gln Gln Leu Gln Ala Cys Val Thr Gln Ala Asn Gln
1               5                   10                  15

Ala Leu Ser Arg Phe Ile Ala Pro Leu Pro Phe Gln Asn Thr Pro Val
            20                  25                  30

Val Glu Ala Met Gln Tyr Gly Ala Leu Leu Gly Gly Lys Arg Leu Arg
        35                  40                  45

Pro Phe Leu Val Tyr Ala Thr Gly Gln Met Phe Gly Val Ser Thr Ala
    50                  55                  60

Thr Leu Asp Ala Pro Ala Ala Val Glu Cys Ile His Ala Tyr Ser
65                  70                  75                  80

Leu Ile His Asp Asp Leu Pro Ala Met Asp Asp Asp Leu Arg Arg
            85                  90                  95

Gly Leu Pro Thr Cys His Ile Lys Phe Gly Glu Ala Asn Ala Ile Leu
            100                 105                 110

Ala Gly Asp Ala Leu Gln Ala Leu Ala Phe Ala Ile Ile Ser Asp Ala
        115                 120                 125

Pro Met Pro Glu Val Ala Asp Arg Asp Arg Ile Ala Met Ile Ala Glu
    130                 135                 140

Leu Ala Asn Ala Ser Gly Ile Ala Gly Met Cys Gly Gly Gln Ala Leu
145                 150                 155                 160

Asp Leu Ala Ala Glu Gly Gln Arg Ile Thr Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Asn Thr Leu Pro Ile Leu
        195                 200                 205

Asp Arg Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Asn Lys Ala Arg Asp Leu Ile Glu Asp Ala Arg Gln
            260                 265                 270

```
Ser Leu His Gln Leu Ala Ala Gln Ser Leu Asp Thr Ser Ala Leu Glu
        275                 280                 285

Ala Leu Ala Asn Tyr Ile Ile Gln Arg Asp Lys
        290                 295

<210> SEQ ID NO 8
<211> LENGTH: 299
<212> TYPE: PRT
<213> ORGANISM: Cronobacter turicensis

<400> SEQUENCE: 8

Met Asp Phe Ser Gln Gln Leu Gln Ser Gln Ala Glu Arg Ala Asn Ser
1               5                   10                  15

Ala Leu Gln His Phe Ile Gly Ala Leu Pro Phe Gln Lys Ser Pro Leu
            20                  25                  30

Val Glu Ala Met Leu Tyr Gly Thr Leu Leu Gly Gly Lys Arg Leu Arg
        35                  40                  45

Pro Phe Leu Val Tyr Ala Thr Gly Glu Met Phe Gly Val Asn Pro Thr
    50                  55                  60

Ala Leu Asp Ala Pro Ala Ala Ile Glu Cys Ile His Ala Tyr Ser
65                  70                  75                  80

Leu Met His Asp Asp Leu Pro Ala Met Asp Asp Asp Leu Arg Arg
                85                  90                  95

Gly Gln Pro Thr Cys His Ile Arg Phe Gly Glu Ala Ser Ala Ile Leu
            100                 105                 110

Ala Gly Asp Ala Leu Gln Thr Leu Ala Phe Ser Ile Leu Ser Asp Ala
        115                 120                 125

Pro Met Glu Asn Val Ala Leu Arg Asp Arg Leu Ala Met Val Ser Glu
    130                 135                 140

Leu Ala Lys Ala Ser Gly Val Ala Gly Met Cys Gly Gly Gln Ala Leu
145                 150                 155                 160

Asp Leu Glu Ala Glu Gly Gln Gln Val Asp Leu Asp Ala Leu Glu Arg
                165                 170                 175

Ile His Arg His Lys Thr Gly Ala Leu Ile Arg Ala Ala Val Arg Met
            180                 185                 190

Gly Ala Leu Cys Ala Gly Asp Lys Gly Arg Asp Ala Leu Val Tyr Leu
        195                 200                 205

Asp Ser Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Gln Ala Lys Ala Arg Ser Leu Cys Asp Asp Ala Leu Ala
            260                 265                 270

Ala Leu Ala Pro Leu Lys Ala Gln Ala Leu Asp Thr Ala Thr Leu Glu
        275                 280                 285

Ala Leu Ala Asn Phe Ile Ile Gln Arg Asp Lys
    290                 295

<210> SEQ ID NO 9
<211> LENGTH: 303
<212> TYPE: PRT
<213> ORGANISM: Pectobacterium astrosepticum

<400> SEQUENCE: 9

Met Thr Asp Phe Ser Ala Gln Leu Asn Ala His Tyr Gln Arg Thr Asn
```

```
              1               5                  10                 15
Arg Met Leu Gly His Phe Ile Thr Ser Leu Pro Phe Gln Ser Ser Pro
                    20                 25                 30

Leu Val Asn Ala Met Glu Tyr Gly Ser Leu Leu Gly Gly Lys Arg Leu
                    35                 40                 45

Arg Pro Phe Leu Val Tyr Thr Thr Gly Glu Leu Phe Asp Met Pro Leu
     50                 55                      60

Glu Ser Leu Asp Ala Pro Ala Ala Val Glu Cys Ile His Ala Tyr
 65                 70                 75                      80

Ser Leu Ile His Asp Asp Leu Pro Ala Met Asp Asp Asp Leu Arg
                85                 90                  95

Arg Gly Gln Pro Thr Cys His Ile Lys Phe Gly Glu Ala Thr Ala Ile
                    100                105                110

Leu Ala Gly Asp Ala Leu Gln Thr Leu Ala Phe Ser Ile Leu Ala Asp
                    115                120                125

Ala Pro Met Thr Gln Val Ser Asp Arg Asp Arg Leu Ala Met Ile Ser
                    130                135                140

Glu Leu Ala Gln Ala Ser Gly Val Ala Gly Met Cys Gly Gly Gln Ala
145                 150                155                160

Phe Asp Leu Glu Ala Glu Gly His Gln Val Asn Leu Ala Ala Leu Glu
                    165                170                175

Arg Ile His Arg His Lys Thr Gly Ala Leu Ile Arg Ala Ala Val Arg
                    180                185                190

Leu Gly Ala Leu Ala Ala Gly Asp Ala Gly Arg Asp Ala Leu Pro Tyr
                    195                200                205

Leu Asp Arg Tyr Ala Asn Ala Ile Gly Leu Ala Phe Gln Val Gln Asp
                    210                215                220

Asp Ile Leu Asp Val Val Gly Asp Ser Ala Thr Thr Gly Lys Arg Gln
225                 230                235                240

Gly Ala Asp Gln Gln Leu Gly Lys Ser Thr Tyr Pro Ser Leu Leu Gly
                    245                250                255

Leu Asp Asn Ala Arg Lys Lys Ala Gln Glu Leu Tyr Gln Glu Ser Leu
                    260                265                270

Ala Ser Leu Asp Asp Leu Val Ala Ser Ser Pro Ile Pro Leu Asn Ile
                    275                280                285

Ala Pro Leu Gln Ala Leu Ala Asn Phe Ile Val Glu Arg Asp Lys
                    290                295                300

<210> SEQ ID NO 10
<211> LENGTH: 312
<212> TYPE: PRT
<213> ORGANISM: Candidatus hamiltonella

<400> SEQUENCE: 10

Met Pro Asp Lys Ile Ser Phe Ser Asp Gln His Thr Ser Phe Asp Phe
 1               5                   10                 15

Asp Gln Gln Leu Ser Lys Tyr Gln Lys Arg Val Glu Thr Tyr Leu Ser
                    20                 25                 30

Ser Ala Leu Asp Lys Leu Pro Ala Tyr Asn Thr Val Leu Leu Asp Val
                    35                 40                 45

Met Arg Tyr Ser Thr Leu Met Gly Gly Lys Arg Leu Arg Pro Tyr Leu
     50                 55                      60

Val Tyr Ala Thr Gly Gln Met Leu Gly Leu Ser Leu Ser Asn Leu Asp
 65                 70                 75                      80

Ala Pro Ala Ala Ala Ile Glu Cys Ile His Ser Tyr Ser Leu Leu His
```

```
            85                  90                  95
Asp Asp Leu Pro Ser Met Asp Asn Asp Asp Leu Arg Arg Gly Glu Leu
                100                 105                 110

Thr Gly His Val Lys Phe Gly Glu Ala Asn Ala Ile Leu Ala Gly Asp
            115                 120                 125

Ser Leu Gln Ser Leu Ala Phe Ser Ile Leu Ala Asp Asp Arg Met Pro
    130                 135                 140

Asp Val Val Thr Glu Asp Arg Leu Ala Met Leu Ser Glu Leu Ala Arg
145                 150                 155                 160

Ala Ser Gly Ala Thr Gly Met Cys Gly Gly Gln Ala Leu Asp Met Ala
                165                 170                 175

Ser Glu Tyr Leu Asp Ile Ser Leu Glu Thr Leu Glu Leu Ile His His
            180                 185                 190

His Lys Thr Gly Ala Leu Leu Arg Ala Ala Val Arg Leu Gly Ala Leu
        195                 200                 205

Ala Ala Gly Glu Thr Gly Arg Lys Ala Leu Pro Trp Leu Asp Gln Tyr
    210                 215                 220

Ala Lys Ser Ile Gly Leu Ala Phe Gln Val Gln Asp Asp Ile Leu Asp
225                 230                 235                 240

Glu Ile Gly Glu Ala Arg Lys Thr Gly Lys Lys Pro Lys Ser Asp Gln
                245                 250                 255

Gln Arg Gly Lys Ala Thr Tyr Pro Gly Leu Leu Ser Leu Lys Gly Ala
            260                 265                 270

Gln Lys Lys Met Ala Ala Leu Tyr Gln Ser Ser Leu Ser Ala Leu Thr
        275                 280                 285

Val Pro Glu Ala Ser Val Tyr Asn Thr Leu Pro Leu Gln Ala Cys Ala
    290                 295                 300

His Phe Ile Leu Glu Arg His Tyr
305                 310

<210> SEQ ID NO 11
<211> LENGTH: 297
<212> TYPE: PRT
<213> ORGANISM: Laribacter hongkongensis

<400> SEQUENCE: 11

Met Thr Asp Thr Asp Phe Leu Arg Trp Met Thr Asp Ile Gln Gln His
1               5                   10                  15

Val Glu Thr Ala Leu Ala Ala Ser Leu Pro Ala Gly Thr His Ala Ala
            20                  25                  30

Thr Pro Leu Phe Asp Ala Met Arg Tyr Ala Ala Leu Asp Gly Gly Lys
        35                  40                  45

Arg Val Arg Pro Leu Leu Val Phe Ala Ala Gly Asp Val Ser Gly Ala
    50                  55                  60

Thr Pro Glu Ala Leu Ser Ala Ala Ala Cys Ala Val Glu Cys Ile His
65                  70                  75                  80

Ala Tyr Ser Leu Val His Asp Asp Leu Pro Cys Met Asp Asp Asp Val
                85                  90                  95

Leu Arg Arg Gly Lys Pro Thr Cys His Ile Ala His Gly Glu Ala Met
            100                 105                 110

Ala Leu Leu Ala Gly Asp Ala Leu Gln Ala His Ala Phe Glu Leu Leu
        115                 120                 125

Ala Ile Pro Leu Pro Gly Val Val Pro Ala Arg Gln Leu Ala Met Val
    130                 135                 140

Ser Ala Leu Ala His Ala Ala Gly Pro Arg Gly Met Cys Gly Gly Gln
```

```
                145                 150                 155                 160
Ala Ile Asp Leu Ala Ala Val Gly His Ala Leu Asp Gln Thr Ala Leu
                165                 170                 175

Glu Tyr Met His Cys Leu Lys Thr Gly Ala Leu Ile Gln Ala Ala Val
                180                 185                 190

Arg Leu Gly Ala Leu Ala Gly Ser Pro Asp Asp Glu Leu Ala Ala
                195                 200                 205

Leu Asp Arg Tyr Ala Arg Arg Ile Gly Leu Ala Phe Gln Val Ile Asp
                210                 215                 220

Asp Val Leu Asp Cys Glu Ala Asp Ser Ala Thr Leu Gly Lys Thr Ala
225                 230                 235                 240

Gly Lys Asp Ala Ala His Asp Lys Pro Thr Tyr Val Ser Leu Met Gly
                245                 250                 255

Leu Gly Glu Ala Arg Ser Tyr Ala His Ala Leu Leu Ala Asp Ala His
                260                 265                 270

Glu Ala Leu Ala Leu Phe Gly Ala Arg Ala Arg Arg Leu Gln Gln Leu
                275                 280                 285

Ala Asp Tyr Ile Val Ala Arg Ser Phe
                290                 295

<210> SEQ ID NO 12
<211> LENGTH: 295
<212> TYPE: PRT
<213> ORGANISM: Pseudomonas aeruginosa

<400> SEQUENCE: 12

Met Ile Ala Ala Tyr Gln Ala Arg Cys Gln Ala Arg Val Asp Ala Ala
1                   5                   10                  15

Leu Asp Ala Leu Phe Val Ala Pro Arg Glu Glu Leu Gln Arg Leu Tyr
                20                  25                  30

Glu Ala Met Arg Tyr Ser Val Met Asn Gly Gly Lys Arg Val Arg Pro
                35                  40                  45

Leu Leu Ala Tyr Ala Ala Cys Glu Ala Leu Gly Gly Ala Pro Gln Arg
                50                  55                  60

Ala Asp Ala Ala Ala Cys Ala Val Glu Leu Ile His Ala Tyr Ser Leu
65                  70                  75                  80

Val His Asp Asp Leu Pro Ala Met Asp Asp Asp Leu Arg Arg Gly
                85                  90                  95

Gln Pro Thr Thr His Arg Ala Phe Asp Glu Ala Thr Ala Ile Leu Ala
                100                 105                 110

Ala Asp Gly Leu Gln Ala Leu Ala Phe Glu Val Leu Ala Asp Thr Arg
                115                 120                 125

Arg Asn Pro Gln Glu His Ala Val Cys Leu Glu Met Leu Thr Arg Leu
                130                 135                 140

Ala Arg Ala Ala Gly Ser Ala Gly Met Val Gly Gly Gln Ala Ile Asp
145                 150                 155                 160

Leu Gly Ser Val Gly Val Ala Leu Asp Gln Ala Ala Leu Glu Val Met
                165                 170                 175

His Arg His Lys Thr Gly Ala Leu Ile Glu Ala Ser Val Arg Leu Gly
                180                 185                 190

Ala Leu Ala Ser Gly Arg Ala Glu Pro Ala Ser Leu Ala Ala Leu Glu
                195                 200                 205

Arg Tyr Ala Glu Ala Ile Gly Leu Ala Phe Gln Val Gln Asp Asp Ile
                210                 215                 220

Leu Asp Val Glu Ser Asp Thr Ala Thr Leu Gly Lys Thr Gln Gly Lys
```

```
                225                 230                 235                 240
Asp Gln Ala His Asn Lys Pro Thr Tyr Pro Ala Leu Leu Gly Leu Glu
            245                 250                 255

Ala Ala Lys Gly Tyr Ala Leu Glu Leu Arg Asp Leu Ala Leu Ala Ala
            260                 265                 270

Leu Asp Gly Phe Pro Pro Ser Ala Asp Pro Leu Arg Gln Leu Ala Arg
            275                 280                 285

Tyr Ile Val Glu Arg Arg Asn
            290                 295

<210> SEQ ID NO 13
<211> LENGTH: 300
<212> TYPE: PRT
<213> ORGANISM: Mannheimia succiniciproducens

<400> SEQUENCE: 13

Met Met Arg Leu Met Tyr Gln Phe Ser Asn Asp Leu Gln Gln Ala Gln
1               5                   10                  15

Gln Arg Ile Asn Arg Phe Leu Glu Ala Gln Phe Asp Glu Ile Asn Thr
            20                  25                  30

Arg Pro Ser Pro Leu Ala Asp Ala Met Lys Tyr Gly Leu Leu Leu Gly
        35                  40                  45

Gly Lys Arg Ile Arg Pro Phe Leu Val Tyr Ala Thr Gly Arg Met Leu
50                  55                  60

Gly Ala Asp Thr Ala Gln Leu Asp Tyr Ala Ala Ala Ile Glu Ala
65                  70                  75                  80

Ile His Ala Tyr Ser Leu Ile His Asp Asp Leu Pro Ala Met Asp Asn
                85                  90                  95

Asp Ser Leu Arg Arg Gly Gln Pro Thr Cys His Ile Ala Phe Asp His
            100                 105                 110

Ala Thr Ala Ile Leu Ala Gly Asp Ala Leu Gln Ala Phe Ala Phe Glu
        115                 120                 125

Ile Leu Thr Lys Ser Thr Ala Leu Ser Ala Glu Gln Lys Leu Arg Leu
    130                 135                 140

Ile Gln Val Leu Ser His Asn Ser Gly Val Phe Gly Met Cys Leu Gly
145                 150                 155                 160

Gln Ser Leu Asp Leu Ile Ser Glu His Lys Gln Ile Ser Leu Ser Glu
                165                 170                 175

Leu Glu Gln Ile His Arg Asn Lys Thr Gly Ala Leu Leu Ser Ala Ala
            180                 185                 190

Leu Lys Met Gly Phe Ile Cys Ser Ser His Phe Ala Asp Asn Ala Leu
        195                 200                 205

Glu Ala Lys Leu Asp Arg Tyr Ala Ala Ala Ile Gly Leu Ala Phe Gln
    210                 215                 220

Val Gln Asp Asp Ile Leu Asp Ile Glu Gly Asp Leu Ala Ala Ile Gly
225                 230                 235                 240

Lys Asn Val Gly Ser Asp Leu Glu Ser Asp Lys Ser Thr Tyr Pro Lys
                245                 250                 255

Leu Leu Gly Leu Ala Gly Ala Lys Gln Lys Ala Arg Glu Leu Tyr Val
            260                 265                 270

Ala Ala Val Gly Glu Leu Glu His Leu Pro Phe Asp Thr Thr Ala Leu
        275                 280                 285

Arg Ala Leu Ala Glu Phe Ile Ile Asn Arg Lys Asn
    290                 295                 300
```

-continued

```
<210> SEQ ID NO 14
<211> LENGTH: 295
<212> TYPE: PRT
<213> ORGANISM: Pasteurella multocida

<400> SEQUENCE: 14

Met Tyr Gln Leu Ser Gln Asp Leu Pro Gln Leu Gln Gln Arg Ile Asn
1               5                   10                  15

Thr Phe Leu Ala Gln Gln Leu Asn Val Asp Ser Ser Pro Ser Pro Leu
            20                  25                  30

Ala Glu Ala Met Arg Tyr Gly Val Leu Leu Gly Gly Lys Arg Ile Arg
            35                  40                  45

Pro Phe Leu Val Tyr Ala Thr Gly Arg Met Leu Gly Ala Asp Leu Asn
    50                  55                  60

Gln Leu Asp Tyr Ala Ala Ala Ser Val Glu Ala Val His Ala Tyr Ser
65                  70                  75                  80

Leu Ile His Asp Asp Leu Pro Ala Met Asp Asp Asp His Leu Arg Arg
                85                  90                  95

Gly Gln Pro Thr Cys His Ile Ala Phe Asp His Ala Thr Ala Ile Leu
            100                 105                 110

Ala Gly Asp Ala Leu Gln Ala Phe Ala Phe Glu Ile Leu Thr Gln Ala
            115                 120                 125

Pro Ala Leu Gln Ala Glu Gln Lys Leu Ala Leu Val Gln Thr Leu Ser
    130                 135                 140

Gln Ala Ala Gly Val Lys Gly Met Cys Leu Gly Gln Ser Leu Asp Leu
145                 150                 155                 160

Ile Ser Glu Gln Lys His Ile Ser Leu Ile Glu Leu Glu Gln Ile His
                165                 170                 175

Arg Asn Lys Thr Gly Ala Met Leu Ser Ala Ala Ile Gln Leu Gly Arg
            180                 185                 190

Ile Cys Ser Pro His Phe Lys Asn Asp Thr Leu Ala Gln Gln Leu Gln
        195                 200                 205

Arg Tyr Ser Glu Ala Ile Gly Leu Ala Phe Gln Val Gln Asp Asp Ile
210                 215                 220

Leu Asp Ile Glu Gly Glu Ser Asp Ile Ile Gly Lys Thr Val Gly Ser
225                 230                 235                 240

Asp Leu Leu Ala Asp Lys Ser Thr Tyr Pro Lys Leu Leu Gly Leu Ala
                245                 250                 255

Gly Ala Lys Gln Lys Ala Gln Glu Leu Tyr Gln Asn Ala Ile Ala Glu
            260                 265                 270

Leu Glu Ser Ile Pro Phe Asp Thr Ser Ala Leu Arg Ala Ile Ala Glu
        275                 280                 285

Phe Val Val Asn Arg Lys Ser
290                 295
```